(12) United States Patent
Fichtl García

(10) Patent No.: US 11,654,013 B2
(45) Date of Patent: May 23, 2023

(54) NUCLEO-RETICULAR MULTI-CELL DUAL-SYSTEM EYE IMPLANT

(71) Applicant: Aldo Fichtl García, Mexico City (MX)

(72) Inventor: Aldo Fichtl García, Mexico City (MX)

( * ) Notice: Subject to any disclaimer, the term of this patent is extended or adjusted under 35 U.S.C. 154(b) by 119 days.

(21) Appl. No.: 16/759,723

(22) PCT Filed: Oct. 29, 2018

(86) PCT No.: PCT/MX2018/000115
§ 371 (c)(1),
(2) Date: Apr. 27, 2020

(87) PCT Pub. No.: WO2019/083350
PCT Pub. Date: May 2, 2019

(65) Prior Publication Data
US 2021/0177572 A1    Jun. 17, 2021

(30) Foreign Application Priority Data
Oct. 27, 2017 (MX) ............... MX/a/2017/013845

(51) Int. Cl.
*A61F 2/14* (2006.01)
*A61F 2/00* (2006.01)

(52) U.S. Cl.
CPC ...... *A61F 2/141* (2013.01); *A61F 2002/0081* (2013.01); *A61F 2002/0086* (2013.01);
(Continued)

(58) Field of Classification Search
CPC .......... A61F 2/141; A61F 2/14; A61F 9/0008; A61F 9/0017; A61F 9/00; A61F 2/15;
(Continued)

(56) References Cited

U.S. PATENT DOCUMENTS 2,570,149 A * 10/1951 Noelle ............... A61F 2/141
606/107
2,688,139 A    3/1954 Fritz
(Continued)

FOREIGN PATENT DOCUMENTS

WO    WO-2011042650 A1 *  4/2011  ............. A61F 2/141

OTHER PUBLICATIONS https://en.wikipedia.org/wiki/Polylactic_acid (Year: 2016).*
PCT/MX2018/000115 International Search Report completed Feb. 19, 2019.

*Primary Examiner* — Keri J Nelson
*Assistant Examiner* — Rebecca Lynee Zimmerman
(74) *Attorney, Agent, or Firm* — Venable LLP; Keith G. Haddaway

(57) ABSTRACT

The Nucleo-reticular Multi-cell Dual-system Eye Implant consists of a spherical structure with calculated and variable axial length depending on the needs required by the orbital eye socket, composed of a cell mesh with alternative designs that in turn, makes up the MMM System, in which suturing is provided in any technique, either in cases of evisceration or enucleation. Thanks to its multi-cell structural design, it favors its placement and reduces the risk of migration, extrusion, exposure and extraction. As it is an arrangement with structural holes, it provides a higher percentage of the volume for its vascularization; it also houses inside a Reticular Fibrovascular Core System, which has a structure based on multilevels equipped with micro-reticular tissue and an intra-level communication based on filaments; with the capacity to contain medicines and/or technology by presenting a dual-system of two screw-on pieces, being able to manufacture in different structural designs and biocompatible materials.
The C100 model made of polylactic acid (PLA), an ideal material for implants, consists of 100 oval cells. Since it is
(Continued)

a light eye implant, it prevents depressure due to settlement or gravity and it can be manufactured in any size.

15 Claims, 29 Drawing Sheets

(52) U.S. Cl.
CPC . *A61F 2220/0008* (2013.01); *A61F 2240/004* (2013.01); *A61F 2250/006* (2013.01); *A61F 2250/0067* (2013.01)

(58) Field of Classification Search
CPC ...... A61F 2002/0081; A61F 2002/0086; A61F 2220/0008; A61F 2240/004; A61F 2250/006; A61F 2250/0067; A61L 2430/16

See application file for complete search history.

(56) References Cited

U.S. PATENT DOCUMENTS

| | | |
|---|---|---|
| 4,731,077 A | 3/1988 | Allen |
| 5,584,880 A | 12/1996 | Martinez |
| 5,713,955 A | 2/1998 | Durette |
| 2006/0069434 A1 | 3/2006 | Durette |
| 2007/0191942 A1* | 8/2007 | Perry ................... A61F 2/141 623/4.1 |
| 2008/0046079 A1 | 2/2008 | Coetzee et al. |
| 2010/0121439 A1* | 5/2010 | Perry ................... A61F 2/141 623/4.1 |
| 2012/0129123 A1* | 5/2012 | Yao ................... A61C 8/0089 433/24 |
| 2012/0220917 A1 | 8/2012 | Silvestrini et al. |
| 2014/0107556 A1 | 4/2014 | Garcia et al. |

* cited by examiner

Ref.1
Ref.2
Ref.3

Ref.2

Ref.1

Ref.1

| Weight of the multicell implant manufactured in polylactic acid (density 1.5gr / cm3) per diameter | |
|---|---|
| Millimeters | Grams |
| 12 | .43 |
| 13 | .54 |
| 14 | .65 |
| 15 | .82 |
| 16 | 1.04 |
| 17 | 1.23 |
| 18 | 1.48 |
| 19 | 1.72 |
| 20 | 1.9 |
| 21 | 2.3 |
| 22 | 2.56 |
| 23 | 2.86 |
| 24 | 3.24 |

FIG. 29

NUCLEO-RETICULAR MULTI-CELL DUAL-SYSTEM EYE IMPLANT

This application is a U.S. National Phase of PCT/MX2018/000115, filed Oct. 29, 2018, which claims priority from MX/a/2017/013845, filed Oct. 27, 2017. Each of which is incorporated by reference in it's entirety.

OBJECT OF INVENTION

The present invention finds itself in the field of the Health Sector, specifically in the specialty of Ophthalmology, in which eye implants are used to preserve the volume of the eyeball affected by trauma or disease, which has been intervened by enucleation or evisceration surgeries (the complete removal of the eyeball or the emptying of the eyeball, respectively). In these cases the oculoplastic surgeon places an eye implant (FIG. 1, Ref. 1) in the orbital cavity to obtain an ergonomic base to which an eye prosthesis fits (FIG. 1, Ref. 2) for aesthetic purposes. These procedures should be performed as they fulfill important orthopedic and aesthetic purposes.

The problem of placing eye implants includes migration, extrusion, exposure and the risk of removal of eye implants due to various causes, such as difficulty in suture clamping, allergic reactions to materials, rejection of a foreign body, weight of the implant causing severe depression and/or poor or no vascularization.

The cost of a quality eye implant is high, because most are imported. An implant currently has a price that fluctuated between $300.00 to $700.00USD. For this reason, they are inaccessible to the population of limited resources. There is record of extreme cases of patients who received marbles and even stone used in the decoration for aquariums, with the consequent iatrogenesis.

Currently eye implants are of smooth surfaces, porous surfaces or a combination of both. They have limitations, since in addition to the problems mentioned above, they also present problems with suturing, which have been tried to solve but not efficiently. The Nucleo-reticular Multi-cell Dual-system Eye Implant solves this problem and represents the new generation of implants with the innovation of the MMM system (Muscular Motor Multi-cell) system and in some cases its integration with the FRC (Fibrovascular Reticular Core), since they are endowed with qualitative improvements constituting a novel invention.

BACKGROUND

The Nucleo-reticular Multi-cell Dual-system Eye Implant is novel, as such it does not have a mediate or immediate record. It is the product of years in comparative anatomy research in mammals, whose eye socket is similar. Prototype tests of this implant were carried out, as it is a previously unexplored structure, obtaining successful results, which exceed the functional expectations of devices used in advance. Previous experiences and failed attempts of using proven technologies should be weighted, including the following background: in a study by the Instituto Superior de Medicina, Hospital Luis Díaz Soto (1) it is described that " . . . the loss of the eyeball caused by trauma, diseases, or as surgical sequelae in the treatment of tumors and other conditions is a problem that affects a significant portion of the population. The restoration of these defects has deserved the attention of researchers, physicians and specialists dedicated to this field since ancient times, so special interest has been paid to the development of both biomaterials and surgical and other procedures that allow adequate prosthetic rehabilitation with better aesthetic results for patients. The specialized scientific literature collects countless attempts made with different materials and techniques to achieve these objectives. For more than 100 years, Mules introduced a hollow glass spherical implant into the orbital cavity, and since then, various materials have been tested for this purpose; variable results have been reported and ultimately, in most cases, possible initial successes have not withstood the test of time as adverse responses have been found due to mechanical intolerance, infections, low biocompatibility, among others.

In the contemporary era, with the very development of the science of biomaterials, it has been possible to obtain higher quality products, which have shown more satisfactory results and therefore a more widespread use such as hydroxyapatite(2), high density porous polyethylene (POREX)(3), silicone, the combination of hydroxyapatite with silicone, among others. In particular, hydroxyapatite has achieved remarkable success for these applications, mainly because it has a structure and chemical composition very similar to that of the mineral support of human bone and dental tissue, hence the high biocompatibility demonstrated in its wide clinical use in the last 20 years as a biomaterial of bone implant, for this reason a greater inclination to the use of spherical hydroxyapatite implants is observed, due to their tolerance and their great fibrovascular integration."

In a study related to the above, carried out in 370 patients who had eye implants of three different types placed for 11 years, from 1990 to 2000, the characteristics of "( . . . ) An ideal orbital implant should provide adequate mobility, good aesthetic results and few complications. Many authors (4, 7, 9, 14) have suggested that an implant that is fully integrated into the orbit will minimize the possibility of migration and extrusion. The microporous hydroxyapatite implant meets these requirements and therefore became the most widely used (7) ( . . . )" "Different implant materials have been used; thus the extraocular muscles can be attached to some of them (5). In recent years, porous spherical implants (porous polyethylene and hydroxyapatite) are the most used (6), thanks to advantages such as: biocompatibility, integration, lower extrusion percentage and less incidence of secondary infections (4.7-10)" (4). In this same study, in 2007 when the results were published, it was found that of 143 patients who received a hydroxyapatite implant (HA) 11.9% had complications, a lower percentage than with the other materials.

While the result was improved with porous implants, they still have surgical technical limitations and fibrovascular integration. In the present invention, the Nucleo-reticular Multi-cell Dual-system Eye Implant improves the results with a new design comprising the MMM system with option to integrate the FRC system, consolidating the Dual-system. Its spherical structural shape or calculated axial length, equipped with multicells, aims to be fully integrated into the orbit. For this purpose, its main characteristics are: spherical shape or spherical shape with calculated axial length, multicells with the possibility of integrating a micro-reticular multilevel fibro vascularizing Core, light weight, suturable, vascularizable; it can contain medicines and/or technology, and improves motor skills.

COMPARATIVE BACKGROUND

The present invention in terms of Article 12 sections I, II, III, and 15 of the Industrial Property Act, is a creation whose comparison yields elements that compared with previous models has evident differences, since there is no precedent with the qualities that are intended to be patented, laying the basis for a new generation of implants on previously non-existent conditions, because it is a design and performance not previously explored, from which it derives that the conditions of novelty and creative activity are met, as set out below:

Derived from the prior art search request of file IT/E/2017/001182, corresponding to the application number IT/E/2017/001181, three possible immediate coincidences were found, which by characteristics and qualities differ from the filed patent, in which the proposed Nucleo-reticular Multi-cell Dual-system Eye Implant has novel features that give rise to the comparison set forth:

1.—The U.S. Pat. No. 5,466,259A implant, called "Orbital implant and method", has different qualities and characteristics that do not correspond to the Nucleo-reticular Multi-cell Dual-system Eye Implant, being aware that the "Orbital implant and method implant lacks its own suture cells that the MMM system has as characteristic, which provides immediate vascularization properties that precede the subsequent fibrovascularization and allows the use of free techniques for suturing, which represents novelties that the aforementioned U.S. Pat. No. 5,466,259A implant, called "Orbital implant and method" cannot have due to its structure, because it is simply an implant belonging to a generation of solid porous implants, which lacks a cell and has no interior space usable to contain a fibrovascular nucleo-reticular system or contain drugs and technology, which represents novelties that have not been explored and that the Nucleo-reticular Multi-cell Dual-system Eye Implant has as unique and novel claims.

2.—With regard to the likely coincidence referred to in the investigation carried out in the link: http://www.ghsplasticsurgery.com/implants.php it could be seen that it refers to the existence of patents for eye implants, emphasizing the materials, both hydroxyapatite, Medpor, biocephalic and grafts of cartilaginous material, since this is only about possible materials and techniques of previous generations in smooth and porous implants, of which the Nucleo-reticular Multi-cell Dual-system Eye Implants foreign, since its novel structure allows multiplicity of materials, being preferred polylactic acid (PLA) because such material among other possible, generates the optimal conditions for the manufacturing of the MMM system and its linkage with the FRC system, such conditions are included only in the Nucleo-reticular Multi-cell Dual-system Eye Implant. Due to its capacities and functions, this implant enhances suturing with vertical, horizontal and angular clamping freedoms thereby improving motor skills, immediate vascularizing flow combined with lightness by having a structural void of 61.22% weight reduction compared to solid weight.

3.—U.S. Pat. No. 5,466,258A concerning the "Orbital Implant" refers that it is about: "orbital enucleation implant has a porous polyethylene implant to which the extraocular muscles may be sutured, and adapted to receive an ocular prosthesis on its anterior surface" and can be adapted to receive an eye prosthesis on its previous surface). It should be specified in this regard, that from the analysis of the summary of the patent being discussed, it is about an implant that expressly refers to its use only for cases of enucleation (total loss of the eyeball without availability of sclerotic tissue). In contrast, the Nucleo-reticular Multi-cell Dual-system Eye Implant has the novelty of allowing its use in cases of evisceration and enucleation, for which a range of possibilities that the MMM system provides through poles, nodes and the effective combination thereof in suturing is deployed, unlike the "orbital implant" of U.S. Pat. No. 5,466,258A, only has a muscle binding tab, which is a limitation, so it lacks optimal suturing capacities. In the description, the implant of U.S. Pat. No. 5,466,258A is only porous and has no conditions that guarantee immediate and total vascularization. Further, it differs in that its shape is not compatible with the calculated spherical axial length that in each case is designed according to the specific needs of each patient, which are fulfilled by the Nucleo-reticular Multi-cell Dual-system Eye Implant referred in this application, since it has two systems that interact in different parts of the implant integration process, because the MMM system and the FRC system are unique to the present invention, which represents a novelty and inventive step for the achievement of total integration purposes that only the Nucleo-reticular Multi-cell Dual-system Eye Implant meets. Similarly, the implant corresponding to U.S. Pat. No. 5,466,258A, refers to a solid porous polyethylene material. On the contrary, the Nucleo-reticular Multi-cell Dual-system Eye Implant is a set of systems preferably made of polylactic acid material, which has the possibility of designing cell structures to the outside forming the MMM system and, where applicable, an optimal reticular interior system for fibro vascularization (F.R.C.). The Nucleo-reticular Multi-cell Dual-system Eye Implant is a novel design. The present invention satisfies the needs of patients and health professionals not met to date, therefore, it is novel. The spherical multi-cell structure or calculated axial length structure equipped with two interactive systems, which are the reason for this patent initiative, responds to expectations that in the specialized market had not been achieved with smooth or porous implants, and with the invention of the Nucleo-reticular Multi-cell Duo-system Eye Implant that has a calculated axial length, has conditions for surgery both with and without sclerotic tissue, and the MMM system can be applied independently or with the option to integrating the F.R.C system, thereby exceeding the results obtained to date with other implant options.

In addition to the above mentioned immediate background of the search with a file number of prior art IT/E/2017/001182, to which the application number IT/E/2017/001181 corresponds, the Durette® implant(6) is referred as a comparative background of the intended patent by way of example. It was developed in order to solve some of the above described inherent problems but does not fulfill the needs of patients and surgeons. It is filed under the following premise: "The Durette® implant is a simple alternative which has the best current surgical techniques made of acrylic (PMMA), a durable material. This is an eye implant with a smooth surface for low exposure levels. All models have tunnels to suture the muscles. A mesh of 20 interconnected tunnels allows tissues to invade and integrate into surrounding tissues to prevent migration, forward displacement, and stretching of tissues. Since it has a permanent smooth surface unlike those that are porous and rough, it has no tendency to compromise the tissues that cover it. All have a medial posterior eccentric elongation which adds more volume and gives a better positioning to the front details thus optimizing the coupling with the eye prosthesis" (7).

It should be weighted that the presentation of Durette's model shows deficiencies, and it is also a smooth implant. We found two references that can be observed, first, it limits just one suturing method and second, it has two pieces that are coupled, which is a scheme that generates complications to surgery. The initial Nucleo-reticular Multi-cell Dual-system Eye Implant model of the present invention, C-100 contains a structure of 100 vascularized oval multicells, of which 80 serve specifically to suit any suturing method, with 216 clamping poles with multiple angles, which take advantage of muscles of various lengths, since poles that make up the multicells can be used to hold the sutures with higher operating margins, unlike the 20 tunnels of the Durette® implant.

As for the reason of being manufactured in two pieces, there is no similarity between both implants, because it does not coincide at all with the intention of using a different thread or coupling system to join in half the mentioned 100-cell spherical structure implant. At no time does it come close to the argument that developed the variation in two screwable parts or with implant coupling system claimed herein. The main reasoning is the creation of a system to transport medicines and/or technology in its inner hollow. In conclusion, the structure of the Nucleo-reticular Multi-cell Dual-system Eye Implant is not smooth or porous; it is a new generation of eye implant based on a structural design. In the introduction of a study, it is pointed out that: "Although the effectiveness of high-density hydroxyapatite and polyethylene porous orbital implants is widely documented, there are still complications, the most common of all being implant exposure and the most severe being extrusion and infection. In many of these cases, it appears that these complications are due to a poor or delayed process of fibrovascular proliferation of the implant (1-3). It is for this reason that current research efforts focus on increasing the rate of fibrovascular colonization of the implant by using different biological substances or by modifying surgical materials or techniques (4-6). According to the published series (1-3), it appears that this risk of exposure and extrusion is somewhat higher in cases of evisceration than in those of enucleation. Although they are small series, especially in cases of evisceration, there is no convincing explanation for this difference, although it has been postulated that the sclera itself would act as a barrier that would hinder fibrovascular invasion (7). This experimental study has sought to determine whether there are differences in the rate and pattern of fibrovascular invasion when the evisceration technique is modified by practicing fenestrations in the sclera. This maneuver would not only break the theoretical sclera barrier but, perhaps more importantly, would lead to a greater surgical trauma and increased inflammatory reaction".(8) In the described scenario, the invention that is claimed has noticeable advances and improvements in surgical, clinical and aesthetic results, which mark the relevance of the implant with Muscular Motor Multi-cell (MMM) system (MMM)—with calculated axial length and its integration of a Reticular Fibrovascular Core (F.R.C.) system consolidating the dual-system.

There is a historical background of eye implants and prostheses in remote civilizations, however, we can say that Mulles' implant in 1884 starts the first generation of smooth implants. In 1989, Dr. Perry provides the hydroxyapatite eye implant, marking a second generation of porous eye implants. In 2017, the invention of the subscribed Aldo Fichtl García, proposing the Nucleo-reticular Multi-cell Dual-system Eye Implant, improves the results so far obtained, and it is considered to be the start of the new generation of Multi-cell eye implants, which represents a novelty previously unexplored.

(1) Rev Cubana Ophthalmol 1998; 11(1):5-13
Higher Institute of Military Medicine. Hospital "Luis Díaz Soto"
Hydroxyapatite Porosa HAP-200 as a spherical bioimplant integrated into surgical anophthalmia.
Gildo J. Pérez Blázquez, 1 Ramón González Santos, 2 Luis Acosta Díaz, 3 María E. Solano Bravo, 4 Jorge L. Oliva Acosta, 5 José L. Rodríguez Pérez6
(2) U.S. Pat. No. 6,063,117 PERRY, ARTHUR C.
(3) U.S. Pat. No. 5,466,258 POREX SURGICAL INC.
(4) Vittorino, M., Serrano, F., & Suárez, F. (2007). Enucleation and evisceration: study of 370 cases. Results and complications. Spanish Society of Ophthalmology Archives, 82(8), 495-499. Retrieved on May 20, 2017, from http://scielo.isciii.es/scielo.php?script=sci_arttext&pid=S0365-66912007000800008&lng=es&tlng=es.
(5) OVITT, M and COATES, G. Stereoselective Ring-Opening Polymerization of meso Lactide: Synthesis of Syndiotactic Poly (lactic acid). In: Journal American Chemical Society. (121), 1999; p. 4072-4073
(6) U.S. Pat. No. 7,988,730 B2 JEAN FRANCOIS DURETTE
(7) http://es.oculoplastik.com/implantes-oculares/durette-implant-20-mm-para-enucleacion-y-evisceracion/
(8) Fibrovascular growth in polyethylene porous implants after different evisceration techniques. Experimental study, Dr. Guerra A1, Marcos M2, Vicario M.aJ3, Sierra J4, Peral JI5(1) Associate Professor. Institute of Applied Ophthalmobiology. Medicine School of Valladolid. (2) Degree in Medicine and Surgery. Institute of Applied Ophthalmobiology. Faculty of Medicine of Valladolid. (3) University Nursing Graduate. Río Hortega Hospital in Valladolid. (4) Doctor in Medicine and Surgery. Recoletas Diagnostic Center in Valladolid. (5) Head Professor Holder. Department of Pathological Anatomy. Medicine School of Valladolid.
Classifications
US classification: 623/6.64
International classification: A61L27/56, A61F2/14, A61L27/30, A61L27/34
Cooperative classification: A61F2/141, A61L2430/16, A61L27/306, A61L27/34, A61L27/56
European classification A61L27/34, A61L27/56, A61L27/30R, A61F2/14B

BRIEF DESCRIPTION OF THE INVENTION

The Nucleo-reticular Multi-cell Dual-system Eye Implant with calculated axial length comprising the MMM system along with the FRC Reticular Fibrovascular Core system or without it as an eye implant in the orbital cavity of mammals, consists of a spherical, light structure with calculated axial length, with multi-cell availability, which facilitates the suturing and promotes vascularization and fibrovascularization; improves muscle motor skills and has the ability to carry technology and supply medicines, or, where appropriate, to dock the Reticular Fibrovascular Core System inside, thus optimizing and obtaining the dual-system.

The Nucleo-reticular Multi-cell Dual-system Eye Implant is made of polylactic acid (PLA), an ideal biocompatible material for implants. As it is the lightest eye implant, it prevents implant depression by settlement or gravity. By the characteristics of the Muscular Motor Multi-cell System, it makes easier the suturing technique, its placement, decreases the time in the operating room and reduces the risk of migration, extrusion, exposure and the risk of implant extraction. Since it is a hollow structure, it provides an inner space where the Fibrovascular Nucleo-reticular System can be added, thus consolidating the Dual-system. The achieved organic integration and lower weight, ease of suturing and better vascularization and motor skills accomplish greater success in integrating the implant into the eye socket. It is made in different millimetric and special sizes with possible variation of models, in one piece, in two screw-on pieces, screwable with or without Reticular Fibrovascular Core, or space to contain technology and to supply medicines, with the possibility of varying the structural design and various biocompatible materials.

BRIEF DESCRIPTION OF FIGURES

FIG. 29.—Illustrates the table of implant measurements and weights.

DETAILED DESCRIPTION OF THE INVENTION

Figure 3:
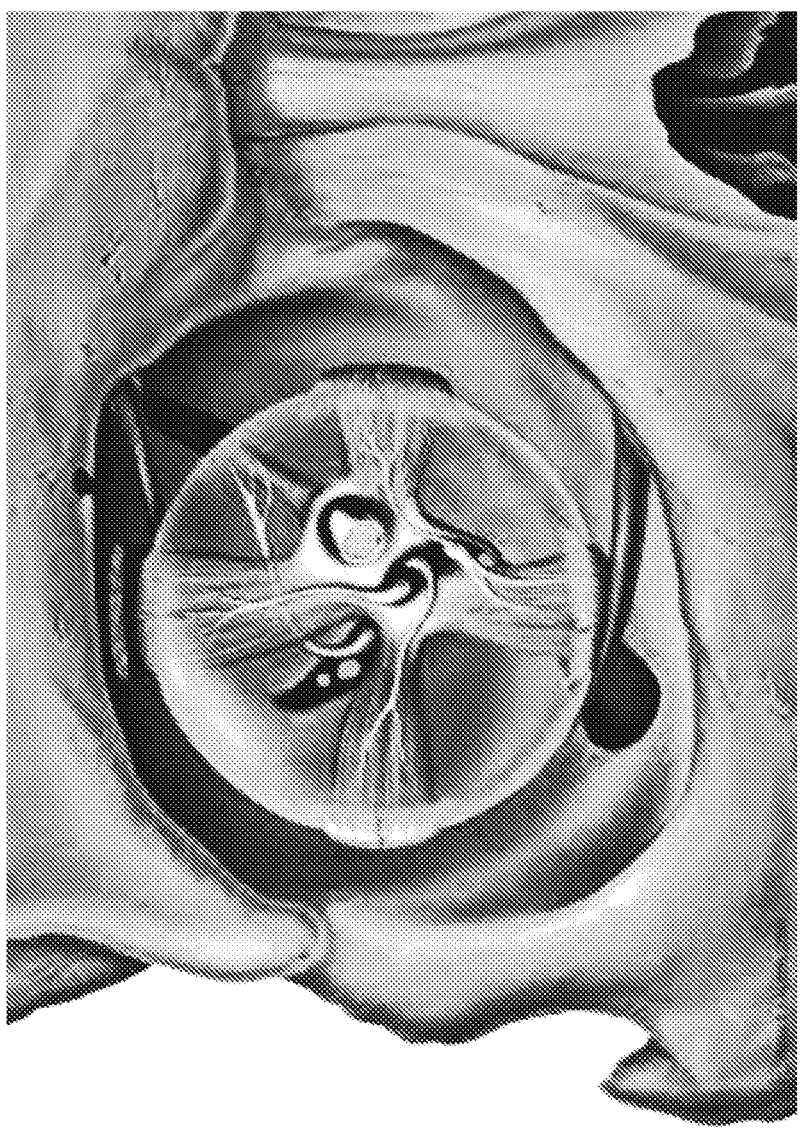
FIG. 3.—Illustrates an eye socket with muscle evidence.
Figure 6:
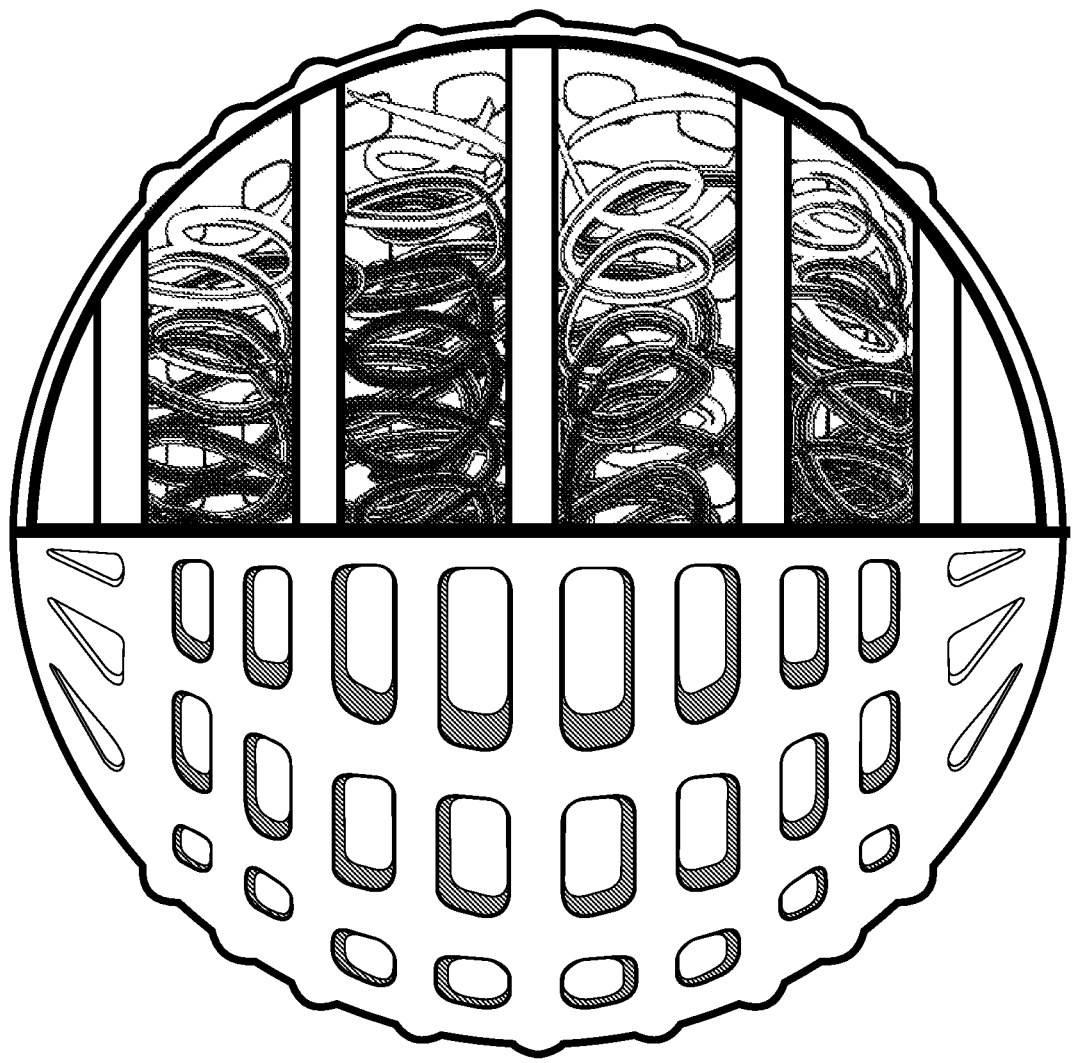
FIG. 6.—Illustrates a longitudinal cutting room where the shape of the nuclear structure, surrounded by the outer structure, is seen.
Figure 14:
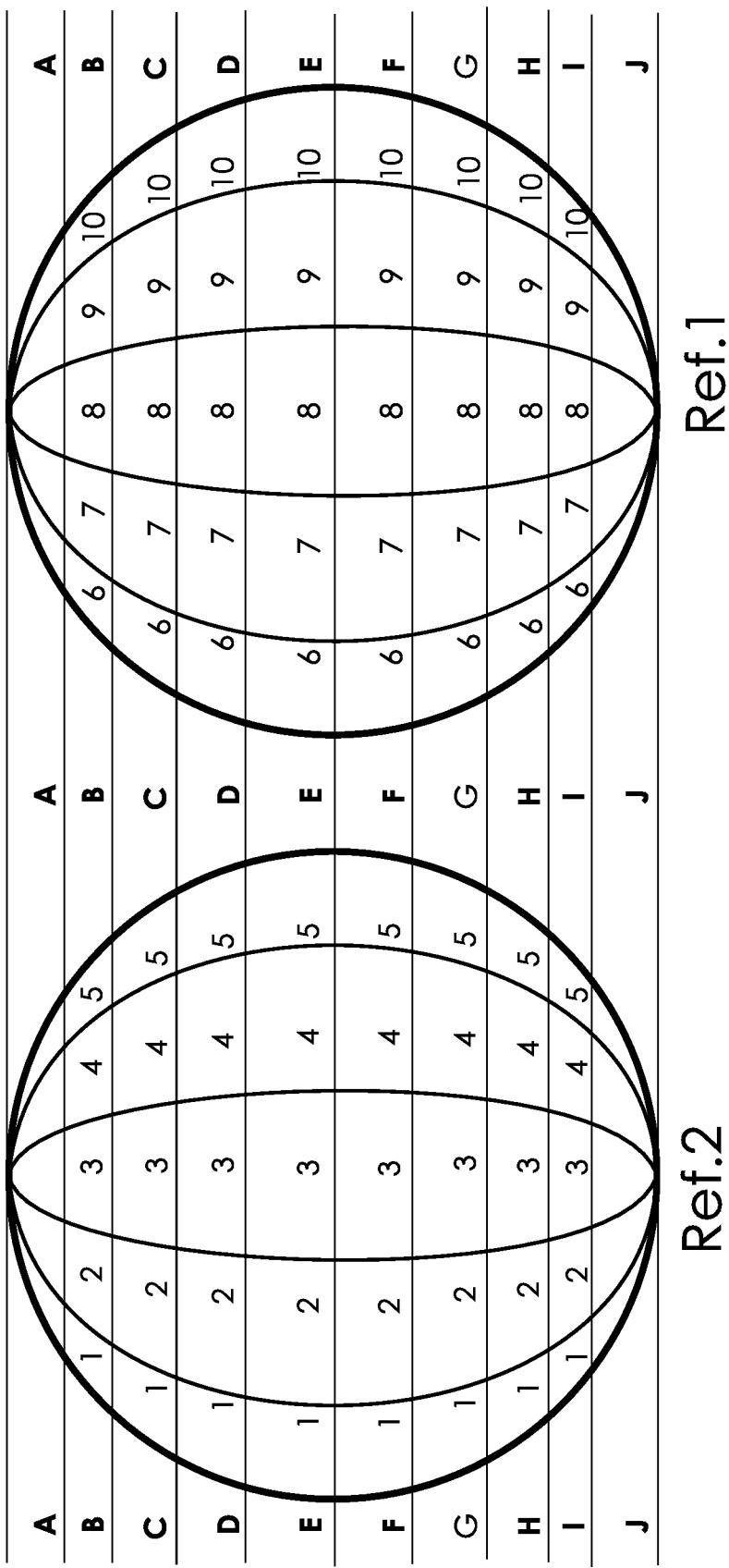
FIG. 14.—Illustrates an example of parallels (Ref. 1) and meridians (Ref. 2) indicated by their respective letters and numbers.
Figure 15:
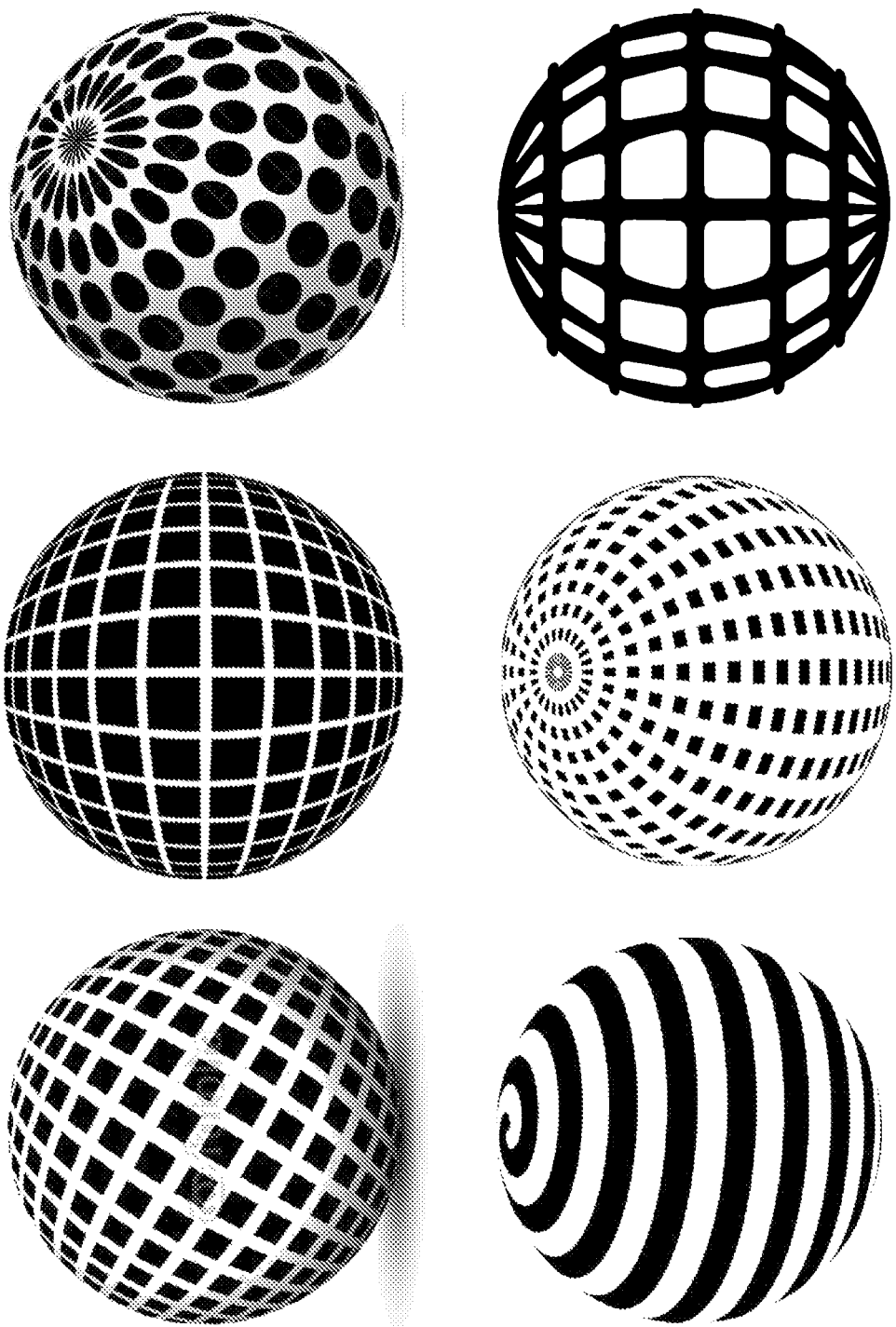
FIG. 15.—Illustrates different forms that can be given to the implant in its Muscular Motor Multi-cell System.
Figure 17:
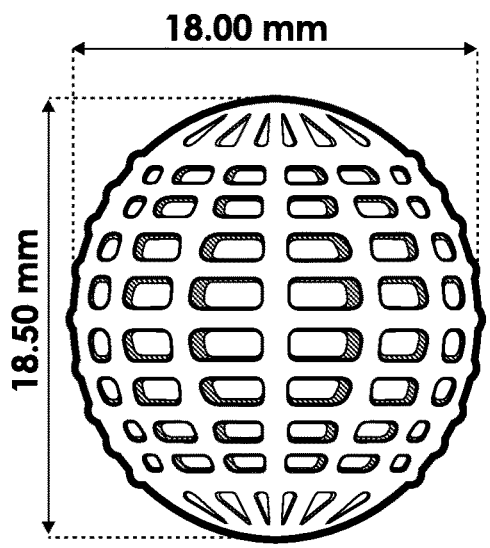
FIG. 17.—Illustrates an Implant with calculated axial length.
Figure 17:
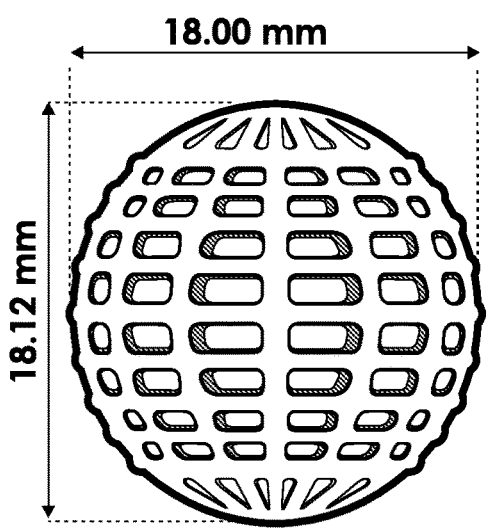
Figure 17:
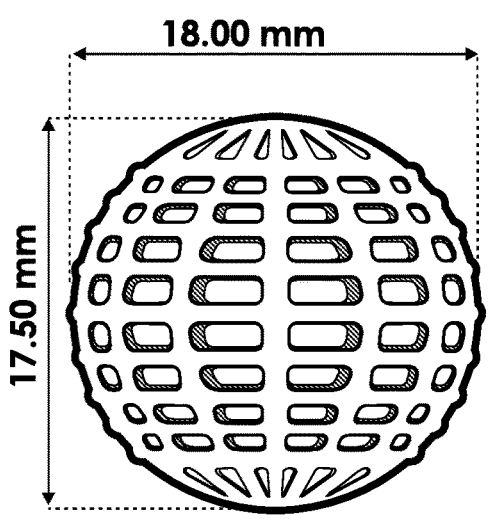
Figure 18:
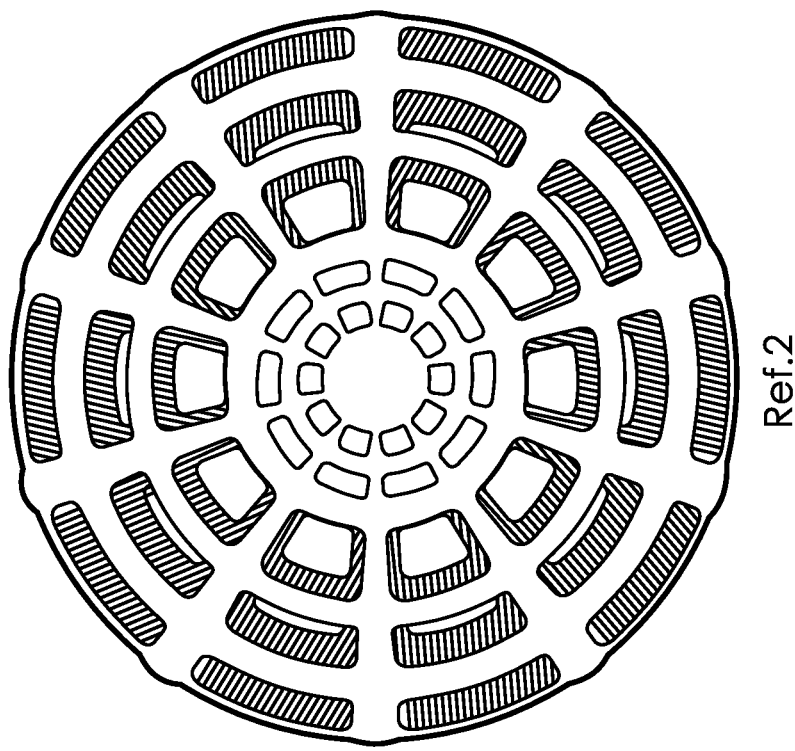
FIG. 18.—Illustrates an image of the C-100 model implant with side (Ref. 1) and frontal (Ref. 2) views.
Figure 18:
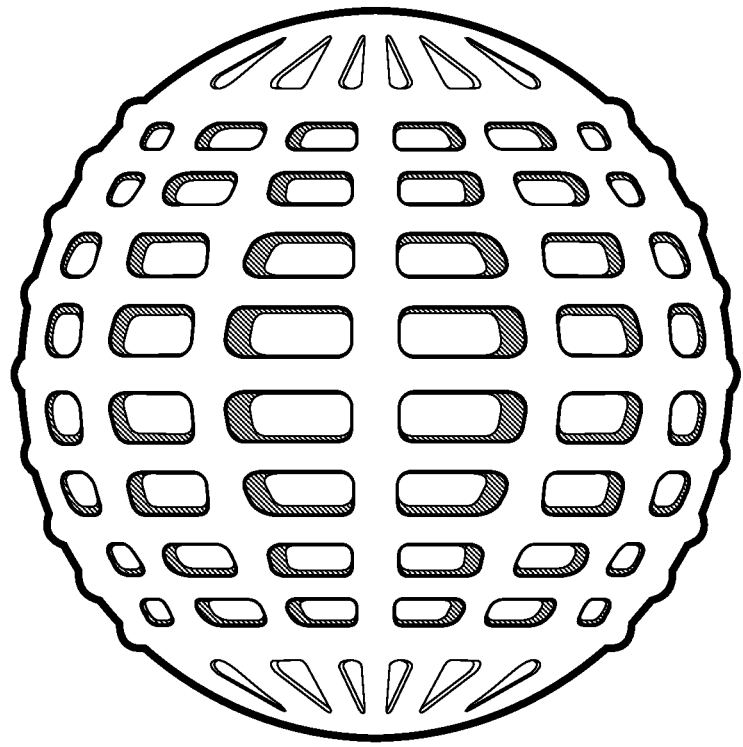

The Nucleo-reticular Multi-cell Dual-system Eye Implant filed in the patent refers to a new generation of multi-cell spherical structures (FIG. 15) with fibrovasculant Core, based on previously unprocessed specifications, both in materials and structure. It has a Muscular Motor Multi-cell System (FIG. 18), with calculated axial length (FIG. 17), and inside a second system called Reticular Fibrovascular Core can be added (FIGS. 6 and 7), thus consolidating the dual-system. Outside, there is a container and clamping system Muscular Motor Multi-cell (MMM), that allows the structural resistance and the possibility of suturing the sclerotic tissue or the muscles available (FIG. 3) to the poles and nodes of the system; the second system called Reticular Fibrovascular Core (F.R.C.) is a multilevel Core capable of favoring and containing vascularization and fibrovascularization made up of micro-reticular levels and intra-level filaments. For the practical purposes of this patent, it is considered appropriate as a method, to refer to the performance of the Nucleo-reticular Multi-cell Dual-system Eye Implant in its model C-100 (FIG. 18, References 1 and 2). The MMM system is the outer structure of the implant, which has a number of functional components, each accurately identifiable, its characteristics are: spherical shape with calculated axial length, equipped with a multi-cell, light, suturable, slip-resistant, vascularizable, fibro vascularizing and motor-enhancing mesh. It is the basic structure on which the cells are distributed throughout and wide, receiving each cell a Cartesian identification (FIGS. 13 and 14), each cell having functions of communicating window. It is a modular structure of variable shape that builds an empty space of canalization, delimited by a perimeter of poles and nodes that make it up with the structural resistance required to be supported in a mesh.

The implant has a spherical structure with calculated axial length, to make the placement easier in the orbital cavity, since anatomically the area where the implant is positioned has an ovoid shape. The MMM system can operate independently of the FRC system, with the option to contain technology or to supply medicines, or conveniently by consolidating the dual system with the interaction of the systems that constitute the patent.

The MMM system can contain a multilevel Core that is designed to achieve the greater integration of the eye implant into the orbital cavity that constitutes the Fibrovascular Reticular Core (FRC) system, from this synergy the so-called dual-system arises.

1.—Muscular Motor Multi-Cell System 1.1 MULTICELLS are the combination of modules in a structure with ideal benefits for the total integration of the implant into the eye socket with facilities for suturable processes, fluid conduction and fibrovascularization. The multi-cell structure of the proposed patent is equipped with structural holes (FIG. 4, Ref. 1), which are arranged as cells (FIG. 4, Ref. 2) in a repeating position and generate optimal conditions for the acceleration of vascularizing integration. The shape and number of cells are due to meet surgical needs with short, medium and long-term results, because they allow the optimal clamping of sclerotic tissue or eye muscle tissues by a variable arrangement of positions, the MMM system has as its basic structure the so-called "cell" which is bordered by poles that at its intersections make up the nodes.

1.2 The Poles

Figure 4:
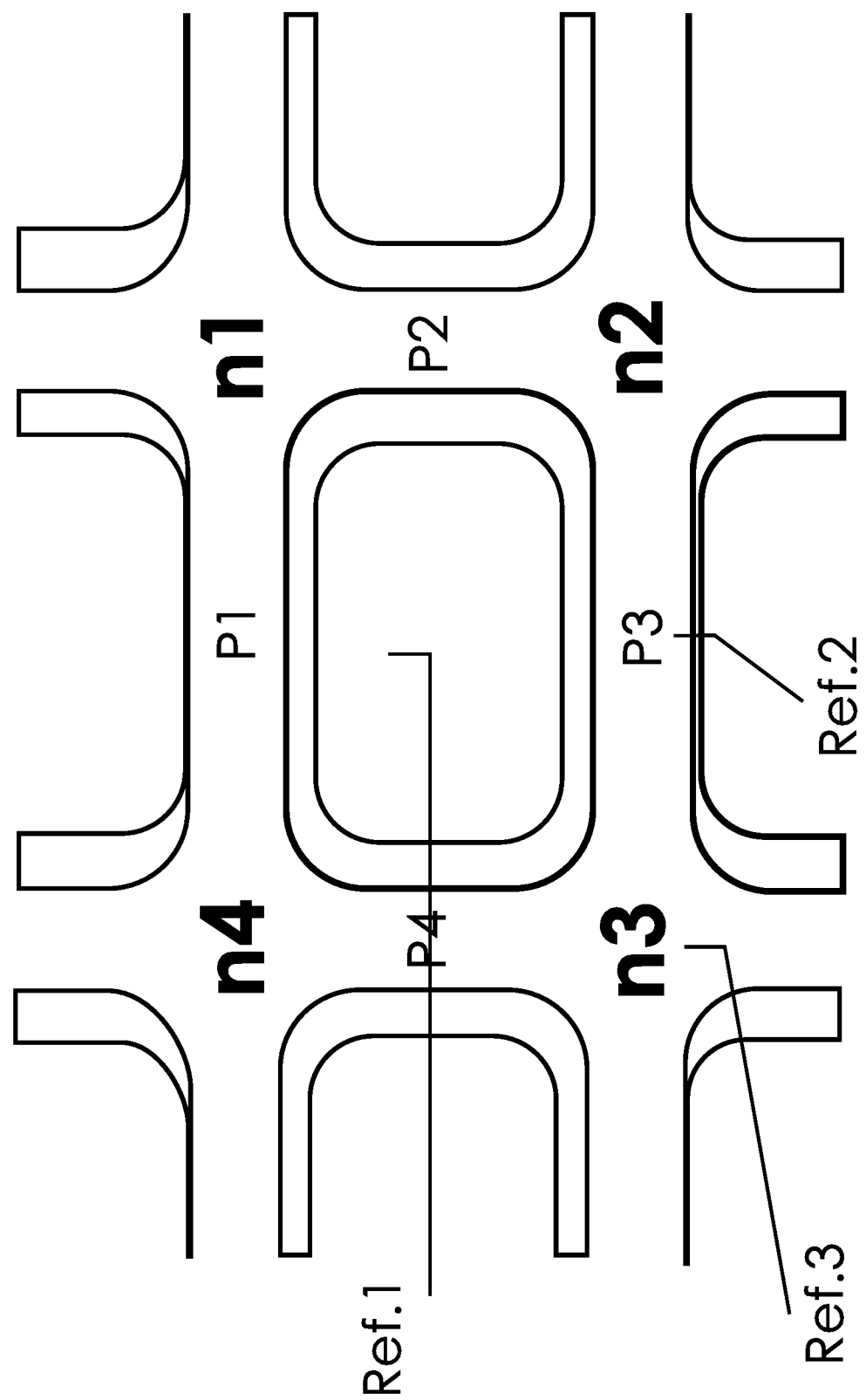
FIG. 4.—Illustrates a view appreciating the cell holes (Ref. 1) with nodes (Ref. 3) and poles (Ref. 2).

The cell consists of perimeter poles, said poles aim to lay solid bases for the predominantly vertical and horizontal suturing, each cell can be endowed with the number of poles that are determined according to the previously estimated structural needs. (FIG. 4, Ref. 2)

1.3 The Nodes

The cross sections of two or more poles make up a structural joint called Node (FIG. 4, Ref. 3), which by its arrangement allows suturing tending to diagonal stresses, which together with the sutures that allow the poles, represents expanding the technical possibilities of suturing.

The number of poles and nodes will depend on the shape that is assigned to the cell, in any case, they enable vertical or horizontal suturing on the poles, diagonal on the nodes or combined, the availability of multicells and their components allows the external system to meet the requirements to improve muscle motor skills.

The availability of cells predisposes the conditions to shorten the intervention times in the operating room, make complicated suturing more viable and allow to accurately identify the procedure followed, with the option of subsequent scheduled operations.

Figure 13:
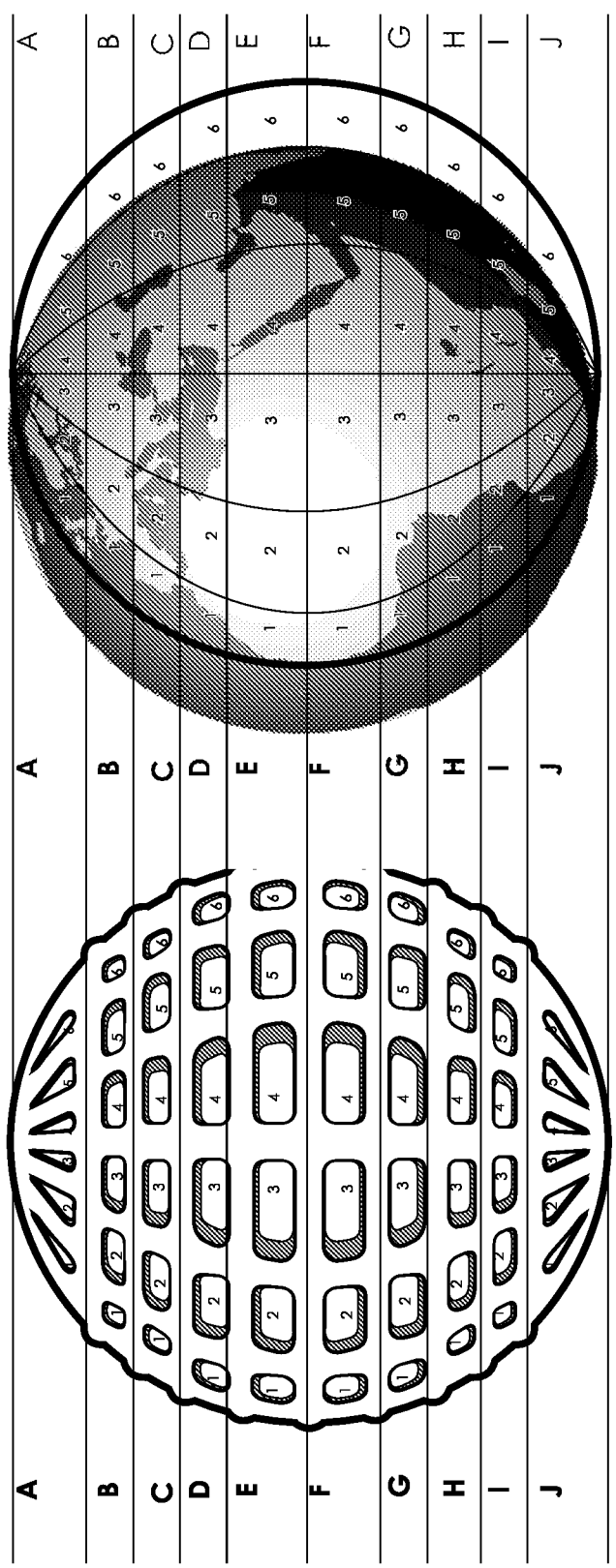
FIG. 13.—Illustrates the similarities of the globe to the implant in terms of its alignments.

The MMM system allows the identification of each of the cells that make up the eye implant, this by means of the Cartesian coordinate system, where the parallels are identified with letters (FIG. 14, Ref. 1) and the meridians with numbers (FIG. 14, Ref. 2), whose signaling is possible by defining the crossing point of each coordinate, being noted with the letter followed by the number. Having a Cartesian similarity to the diagram of the globe (FIG. 13).

Figure 16:
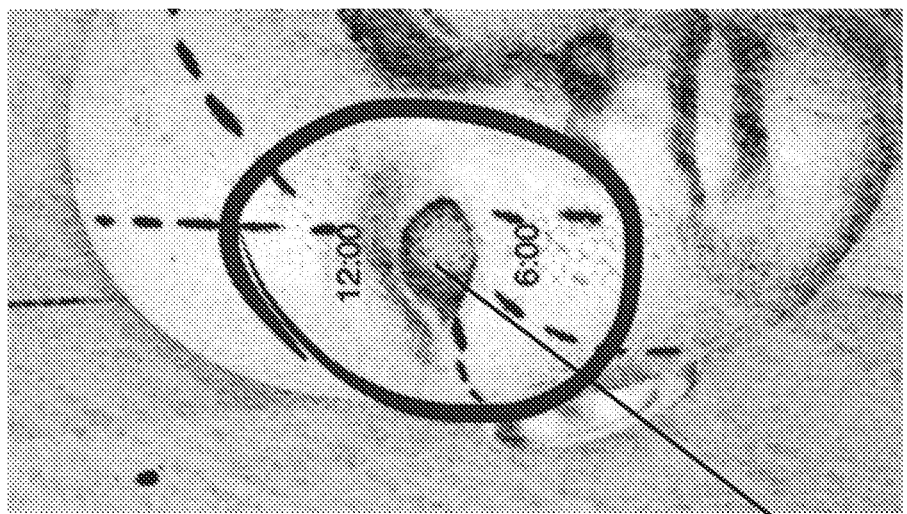
FIG. 16.—Illustrates the placement of the implant in the receiving patient with reference to a clockwise direction to locate de pieces.
Figure 16:
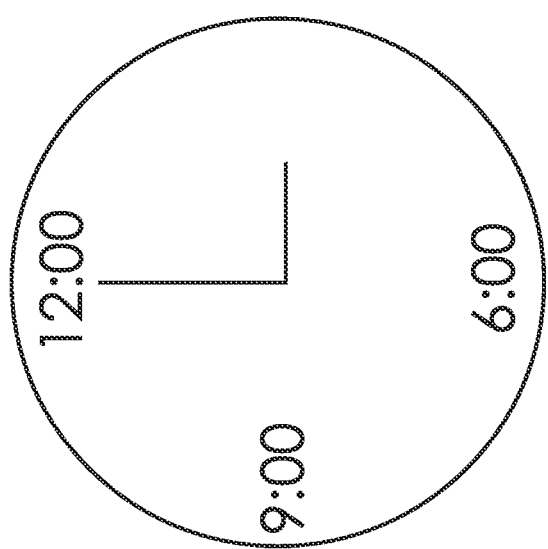

The implant when placed (Ref. 1, FIG. 16), defines in the part that directs to the forehead of the receiving patient, the upper point and accordingly, the corresponding cell is the southern cell (equivalent to number 12 of clock hands) being the count of the meridians (numbers) upstream clockwise and the parallels (letters) upstream from the front point to the rear one of the eye structure (FIG. 16).

2.—Fibrovascular Reticular Core System

The FRC system consists of a multilevel Core, composed of micro-reticular and semi-permeable surfaces, supported by optimal filaments for fibrovascularization. The Core can also contain medicines and/or technology or be replaced by these.

It represents a system designed inside the sphere and aligned to the parallels, it is constituted by a series of multilevels (FIG. 7, Ref. 1) or micro-reticulated, semipermeable platforms, which provide integral structural strength and promote fibrovascular function by having supporting filaments (FIG. 7, Ref. 2) in the spaces between the nuclear multilevels.

Figure 9:
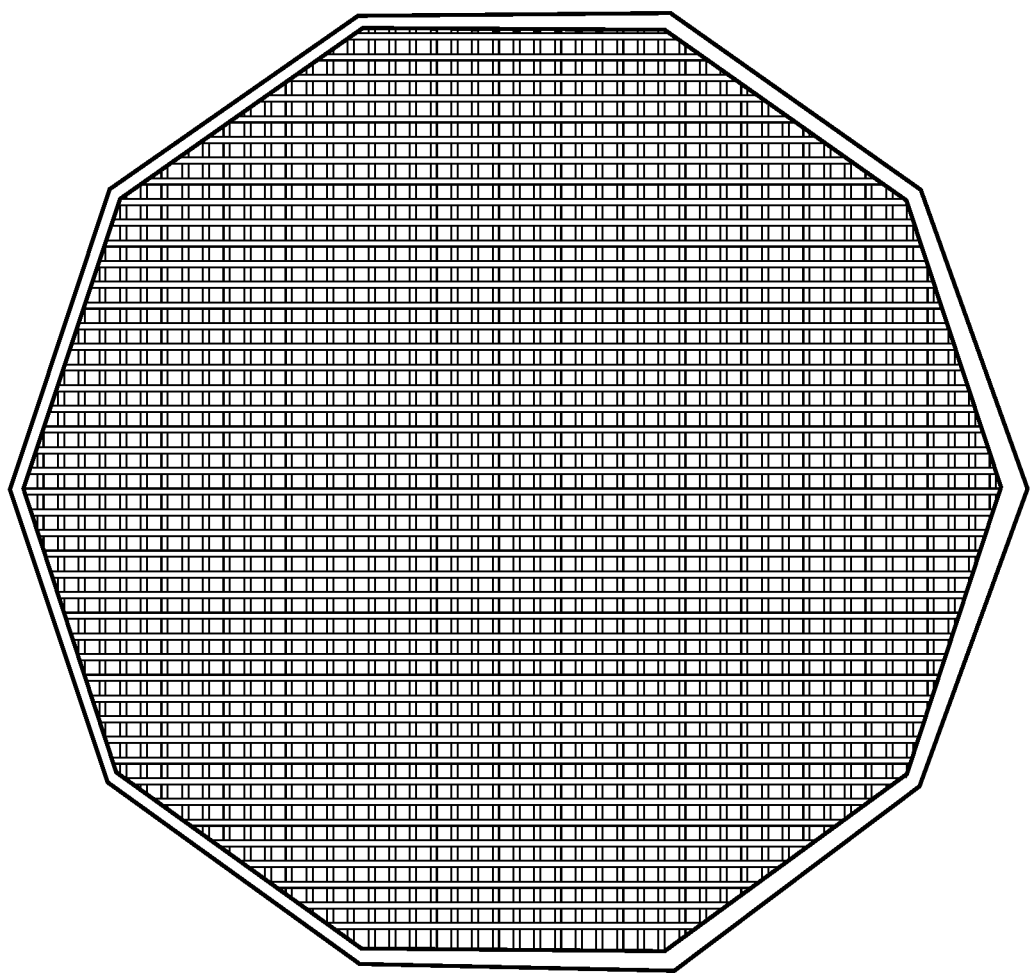
FIG. 9.—Illustrates a view of the Fibrovascular Micro-reticular platform forming the multilevels.
Figure 12:
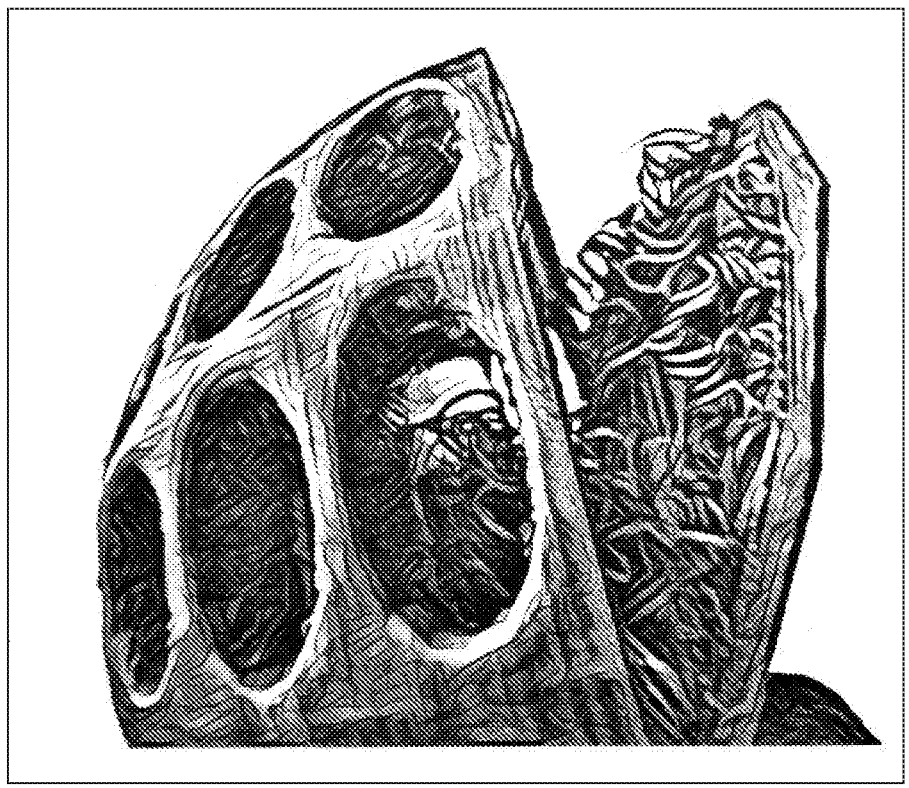
FIG. 12.—Illustrates a longitudinal cut macro photography with a sample of filament availability in the core.

The platforms or multilevel arranged in variable quantity, (according to the number of parallels), are semipermeable structures of vascularizable and integrable base, which are formed and operate because they are a micro-reticular mesh (FIG. 9). In the space between platforms there are supporting filaments that guarantee the fibrovascularization in all inner spaces of the structure (FIG. 12).

2.1 Multilevels

Figure 7:
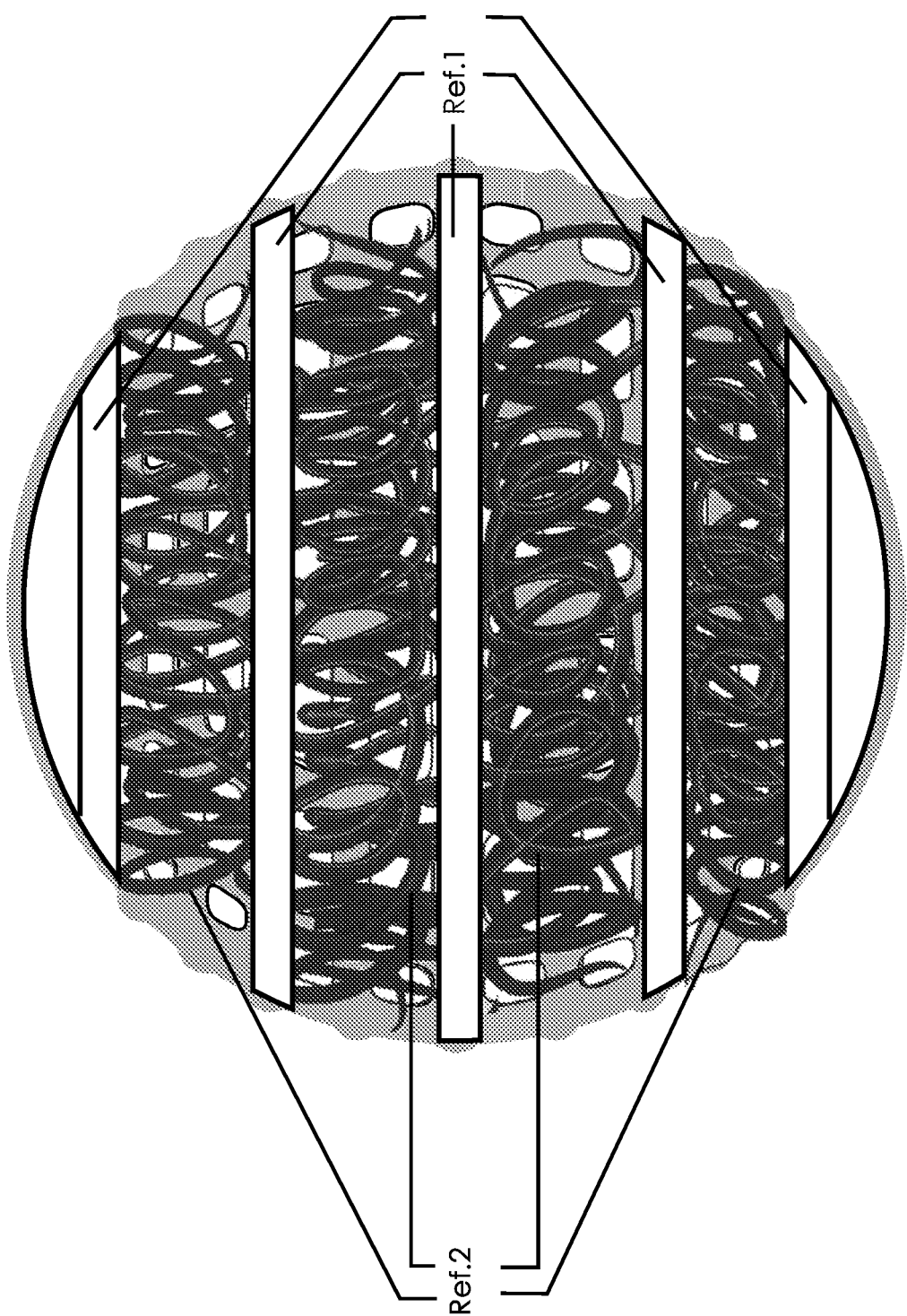
FIG. 7.—Illustrates a cross-section of the multi-cell sphere where the multilevel structure (Ref. 1) and Filaments (Ref. 2) are seen.

They are platforms that in their sum, make up the Core, aligned and fixed to the parallels of the MMM system They are composed of micro-reticular tissue (FIG. 7).

2.2 Micro Reticules.—

They are the tissue that consist of multilevels and has the function of communication of the following strata, their tissue being semipermeable allows to adjust the blood flow and sets the structural basis for the fibrovascular establishment (FIG. 9).

2.3 Filaments

Among the multilevels, a mesh of fibrous structures is laid out; they connect and reinforce each level with the immediate ones through their action, supply the blood flow and by adhesion allow vascularization and accordingly fibrovascularization (FIG. 12).

Light Weight

The Nucleo-reticular Multi-cell Dual-system Eye Implant in its initial C-100 model (FIG. 18), is a light structure due to its design, with multicells that generate free spaces, composed of a mesh of structural forms, which leaves partially free the total surface of the eye implant, achieving less weight, and it can add a structural core to the interior of the sphere, equipped with multi-level spaces with free spaces, achieving the structural lightness that has the objective of avoiding the depression, migration and extrusion of the implant by settlement or gravity.

The dual-system design of the outer multi-cell implant and micro-reticular multi-level core makes the structure of the sphere be composed of greater free spaces due to the presence of outer cellular and reticular nuclear spaces.

Figure 11:
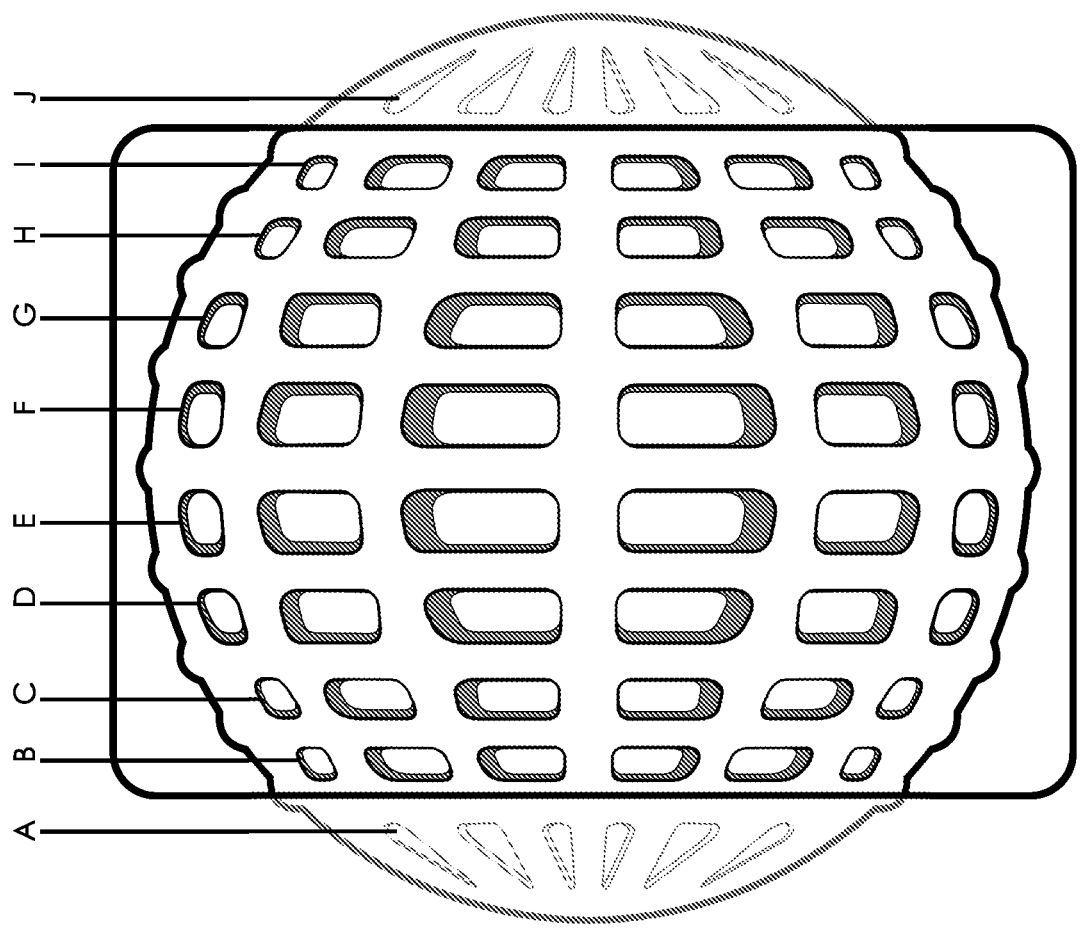
FIG. 11.—Illustrates the usable cells for suturing from parallels B to I.
Figure 20:
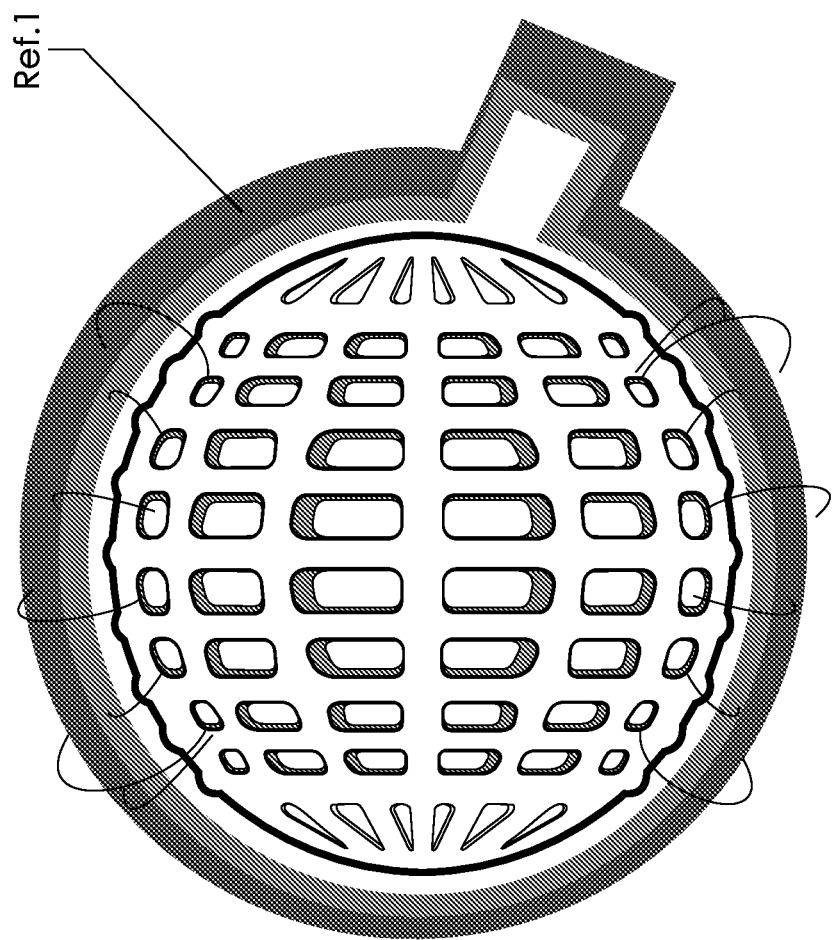
FIG. 20.—Illustrates the Nucleo-reticular Multi-cell Dual-system Eye Implant in case of scleral suture evisceration (Ref. 1).
Figure 21:
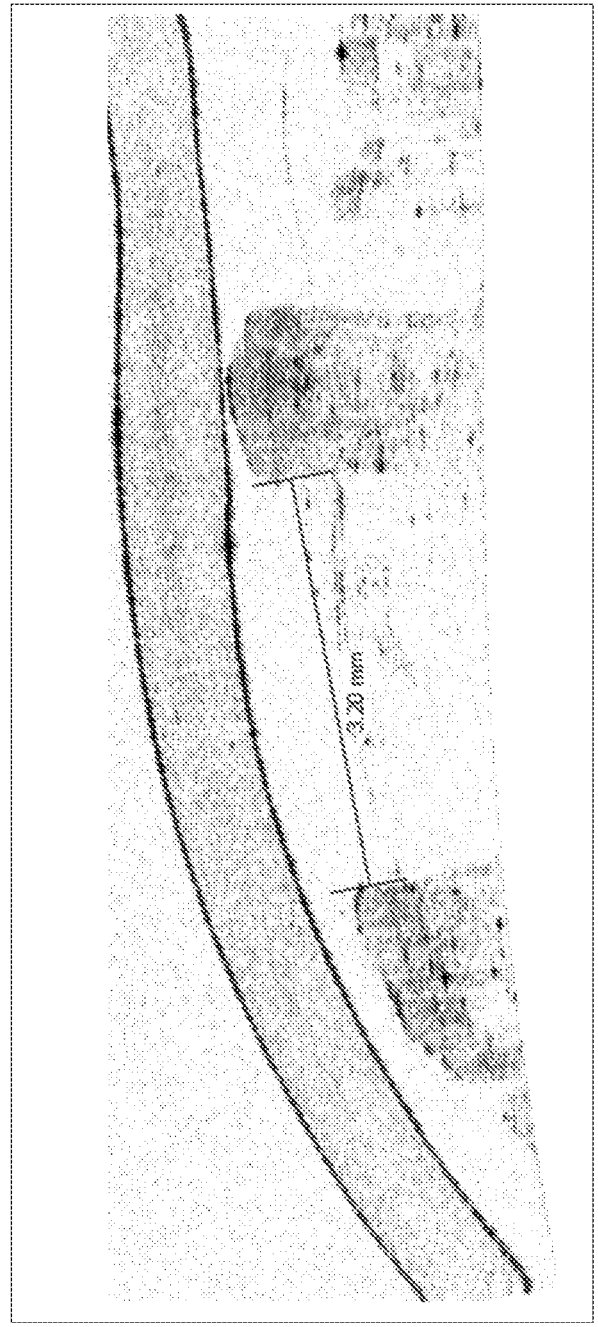
FIG. 21.—Ultrasound image illustrating the cell example in parallels E and F with horizontal measurement in C-100 model of 18 mm.
Figure 22:
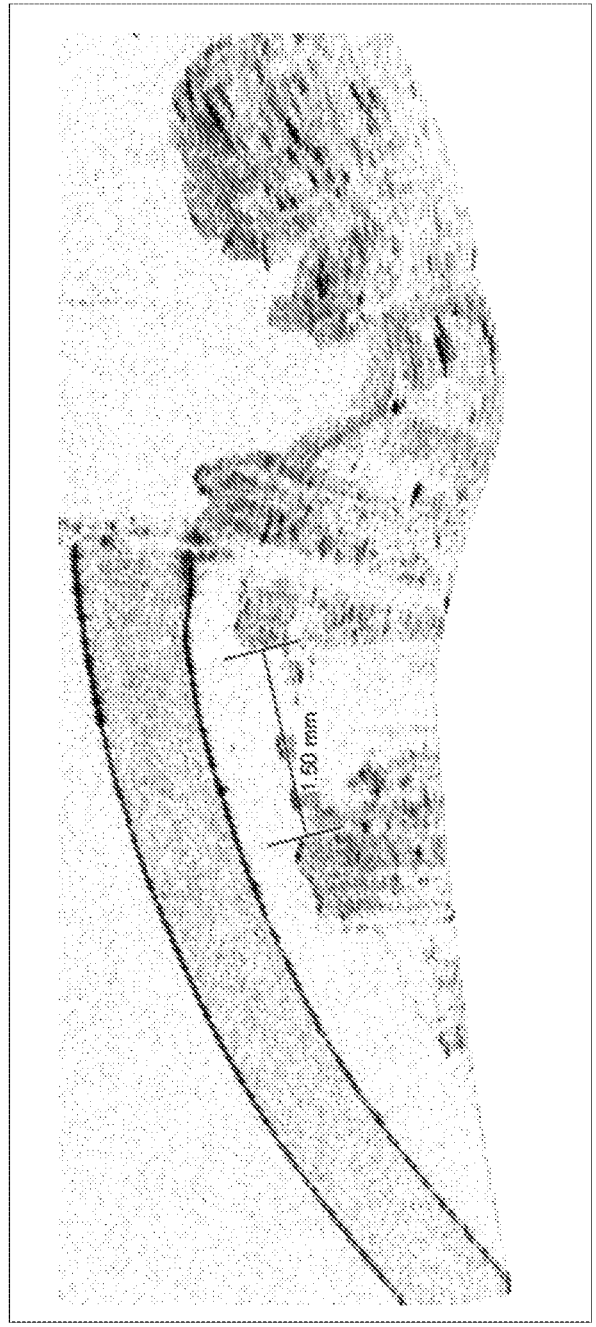
FIG. 22.—Ultrasound image illustrating a cell example in parallels E and F with vertical measurement in model C-100 of 18 mm.
Figure 23:
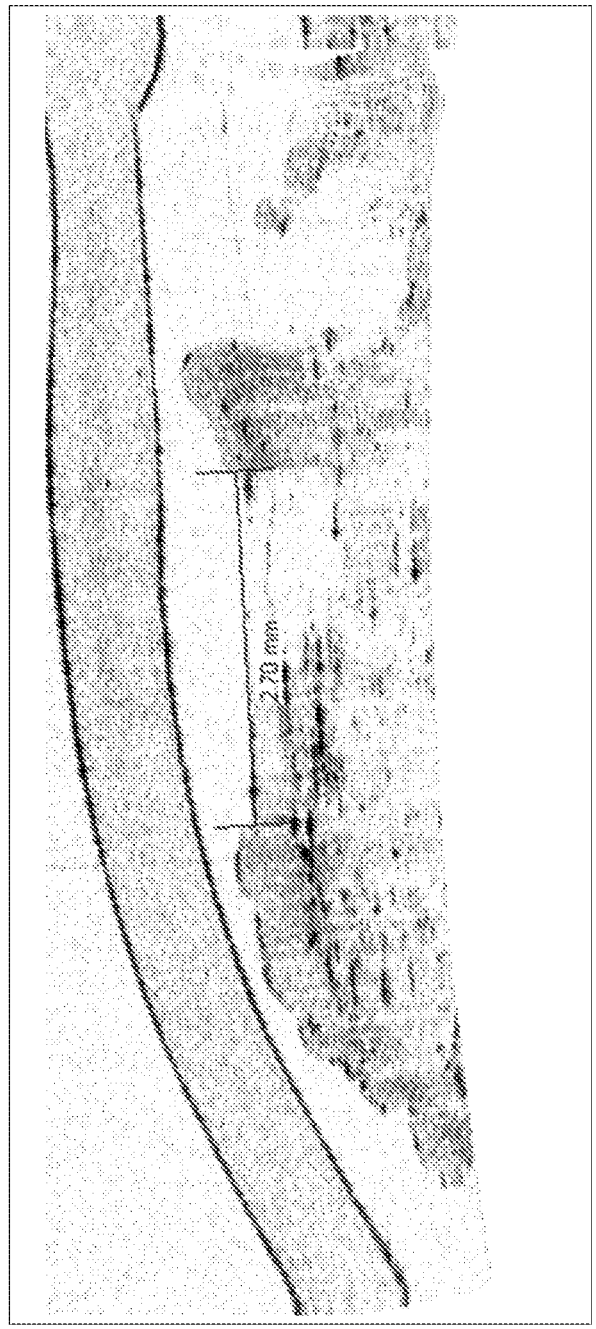
FIG. 23.—Ultrasound image illustrating a cell example in parallels D and G with horizontal measurement model of C-100 of 18 mm.
Figure 24:
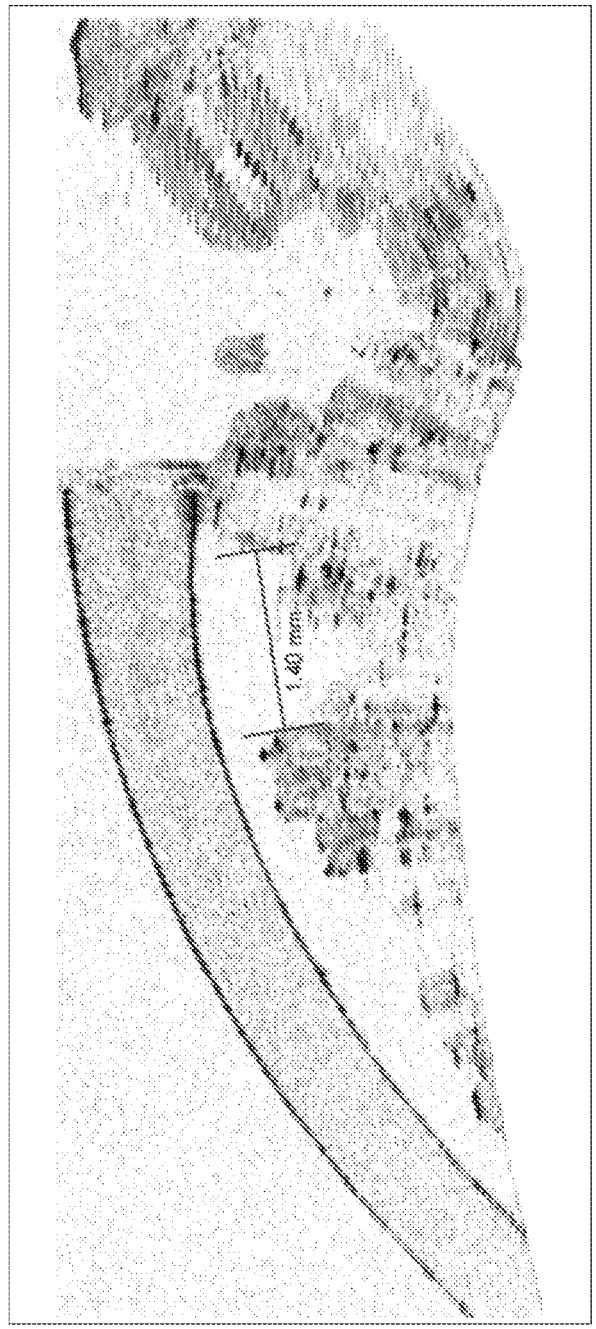
FIG. 24.—Ultrasound image illustrating a cell example in parallels D and G with vertical measurement in model C-100 of 18 mm.

The lightness is appreciated in the implant due to the low density surfaces due to its structure, verbi gratia, it is considered standardized in the matter, taking as an initial reference the implant with a diameter of 18 mm, to that extent, in the model C-100 with design of 100 oval multi-cells, presents in its widest extent 20 cells (E and F) of 3.20 mm by 1.50 mm (FIG. 19, FIG. 20) 20 cells (D and G) of 2.70 mm by 1.40 mm (FIG. 21, FIG. 22); 20 cells (C and H) of 1.75 mm by 1.00 mm (FIG. 23 FIG. 24; 20 cells (B and I) of 0.65 mm by 0.40 mm (FIG. 11).

Regarding the weight, it shows that this initial model of 18 millimeters (mm) in diameter has a volume of 3.05 milliliters (ml). The density of polylactic acid (PLA) is 1.25 grams/cubic centimeter (gr/cm$^3$), if it were a solid sphere, it would weigh 3.81 gr. However, thanks to the multi-cell design and micro-reticular multi-level Core and polylactic acid (PLA) material, a weight of only 1.48 gr is reached, and the percentage obtained for the volume to be vascularized is 61.22%.

For the various measurements of the C-100 implant structure made of polylactic acid (PLA), which has a density of 1.25 gr/cm$^3$, the best measurement-weight ratio results are achieved, which are referred to in the table of FIG. 29.

Regarding the methodology to arrive at the certainty of the coefficients previously set forth, the following equations were performed:

PLA Density—1.25 gr/cm$^3$ $$1 \text{ cm}^3 \times 1 \text{ milliliter}$$

If diameter is 18 mm radius is 9 mm(10 mm×1 cm)=0.9 cm solid volume=sphere volume=$4/3\pi(r^3)$ $4/3\pi(0.9\ cm)^3 \times 3.0536\ cm^3 = 3.0536\ ml$ PLA Solid Sphere Mass $d=m/v$ $m=dv=1.25\ g/cm^3(3.0536\ cm^3)=3.817\ g$ Mass Ratio Celled sphere mass=1.48 g Solid1 sphere mass=3.817 g % by mass is (1.48 g)(100)/3.817 g=38.773% by weight of the celled sphere compared to the solid sphere.

That is, a decrease in:

100−38.773%=61.22% by weight reduction compared to solid weight.

Suturable

Figure 8:
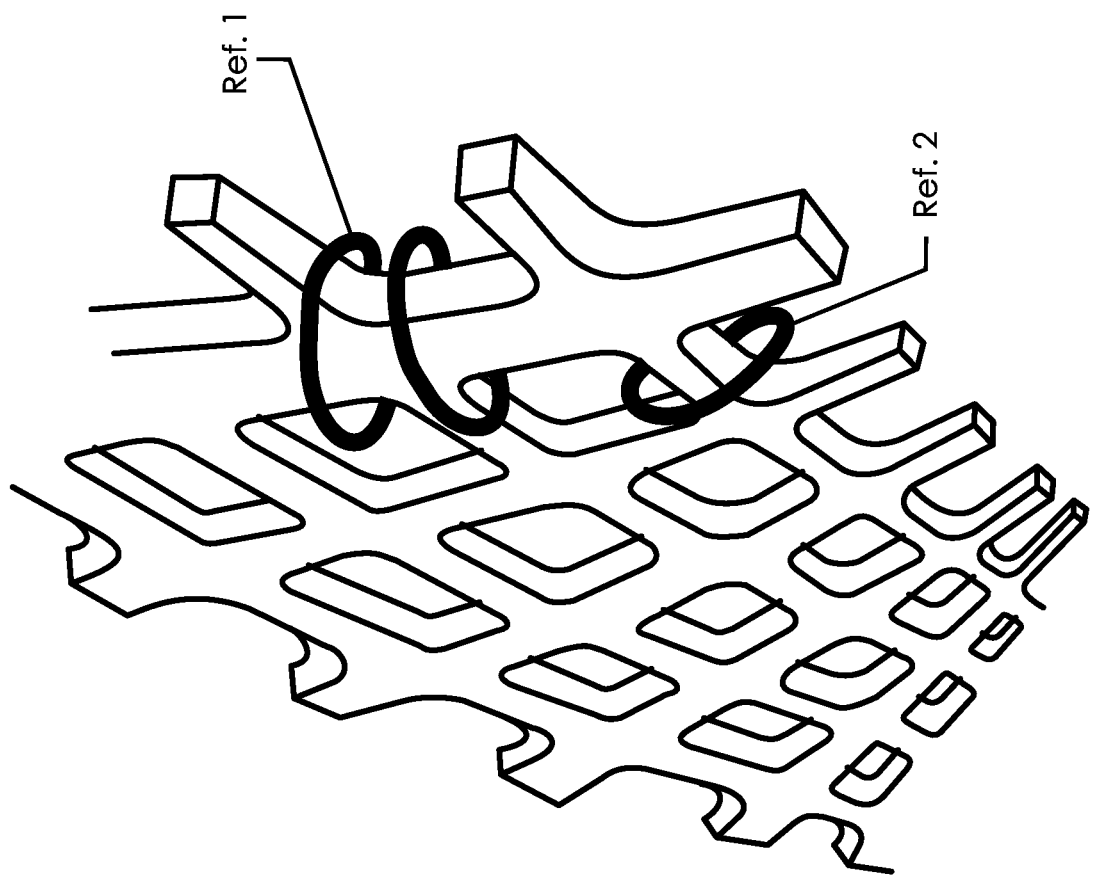
FIG. 8.—Illustrates an example of nodal suture (Ref. 1) and a pole (Ref. 2) in the MMM system.

The Nucleo-reticular Multi-cell Dual-system Eye Implant, in its MMM outer system, is intended to facilitate suturing of the implant to fix the extraocular muscles and the back of the eye socket, due to the design with multicells, poles and nodes available in the required abundance (FIGS. 4, 8 and 11). In this multi-cell structure, practically any suturing method may be used and gives total technical freedom to the acting oculoplastic surgeon. It is ideal in enucleation surgery (FIG. 19) and evisceration (FIG. 20).

Figure 5:
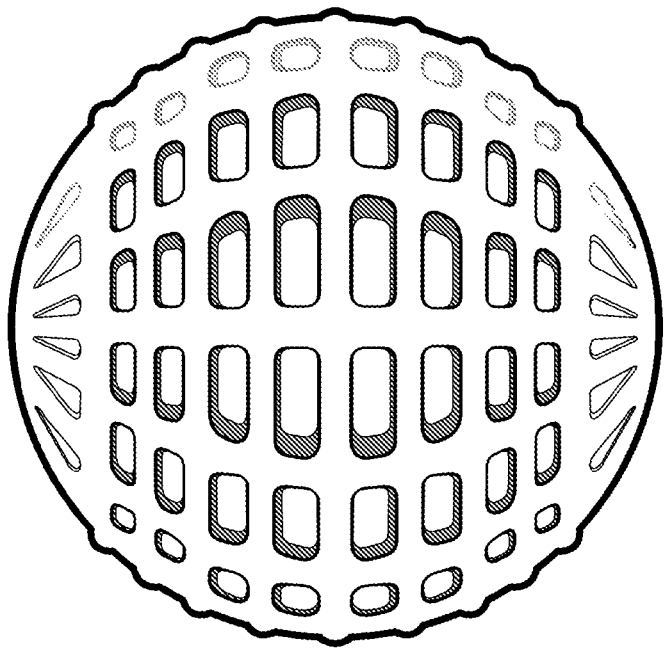
FIG. 5.—It is a graphical representation illustrating both sides of the eye implant where 80 cells (Ref. 1), 150 vertical and transverse poles (Ref. 2), and 70 nodes (Ref. 3) are added.
Figure 5:
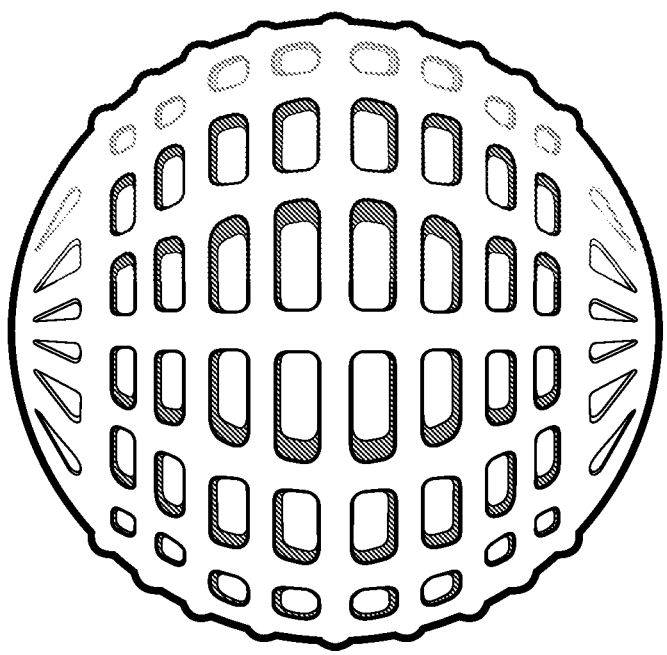

The C-100 model of the present invention comprises a structure of 100 oval multicells, of which 80 (FIG. 5, Ref. 1) serve specifically to adapt to any suturing method, with 150 vertical and transverse poles (FIG. 5, Ref. 2) and 70 clamping nodes (FIG. 5, Ref. 3), with multiple angles suitable for suturing.

Figure 25:
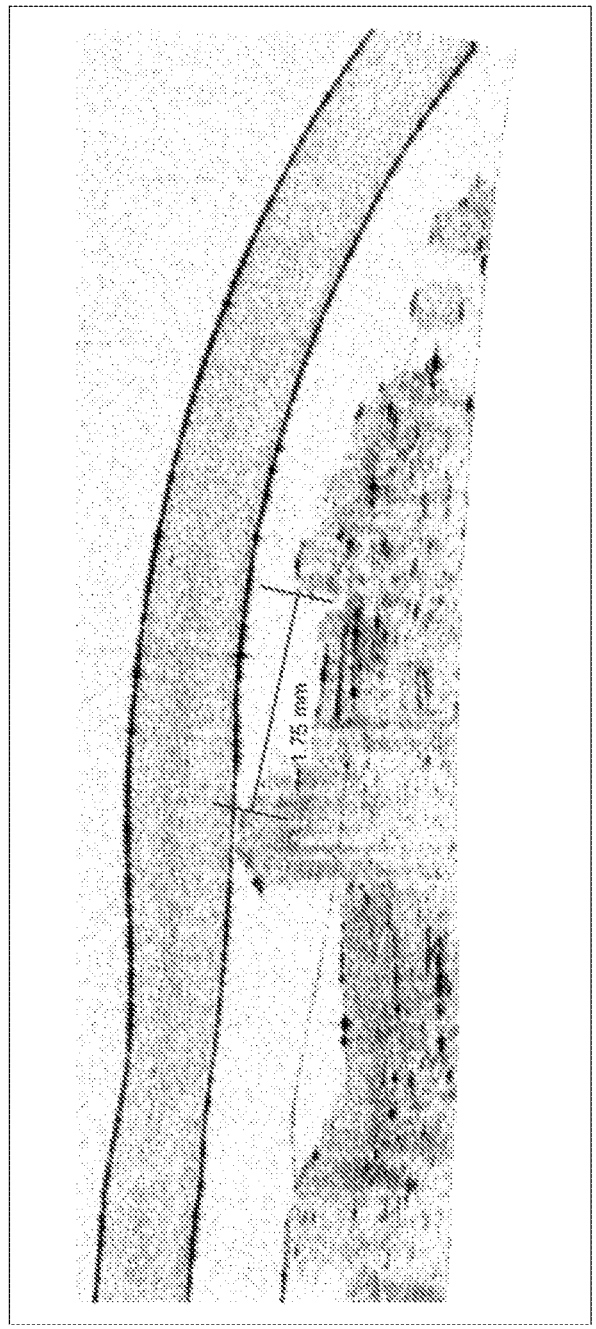
FIG. 25.—Ultrasound image illustrating a cell example in parallels C and H with horizontal measurement model of C-100 of 18.
Figure 26:
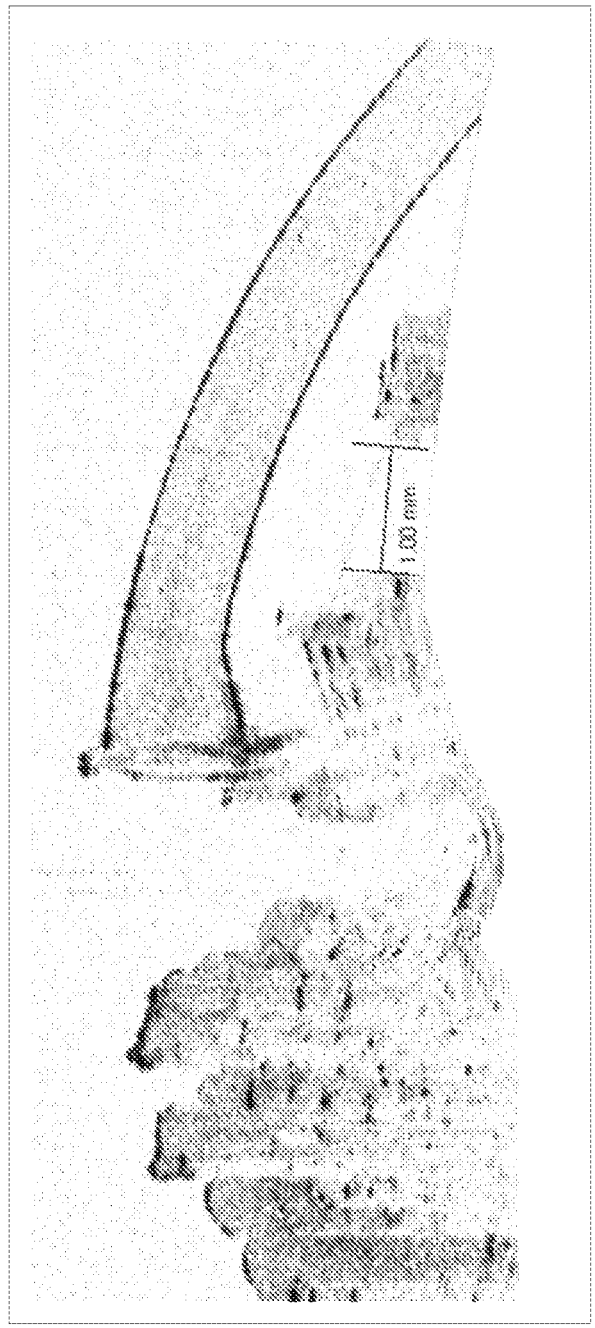
FIG. 26.—Ultrasound image illustrating a cell example in parallels C and H with vertical measurement in model C-100 of 18 mm.
Figure 27:
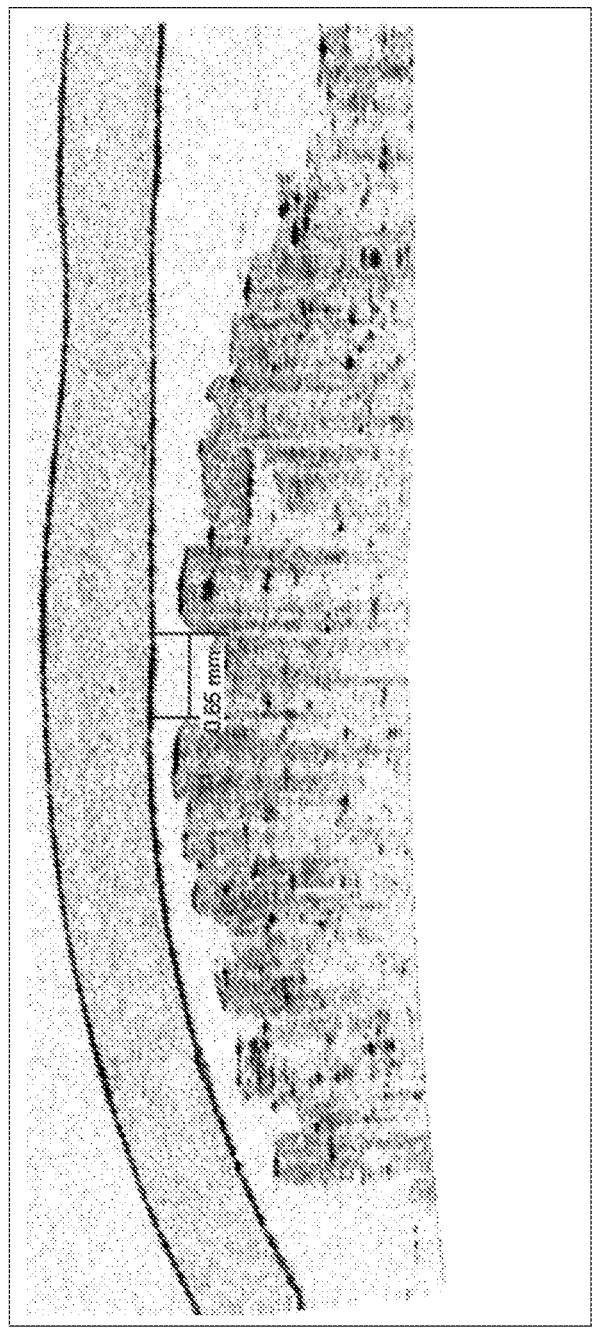
FIG. 27.—Ultrasound image illustrating a cell example in parallels B and I with horizontal measurement in C-100 model of 18 mm in its widest size.
Figure 28:
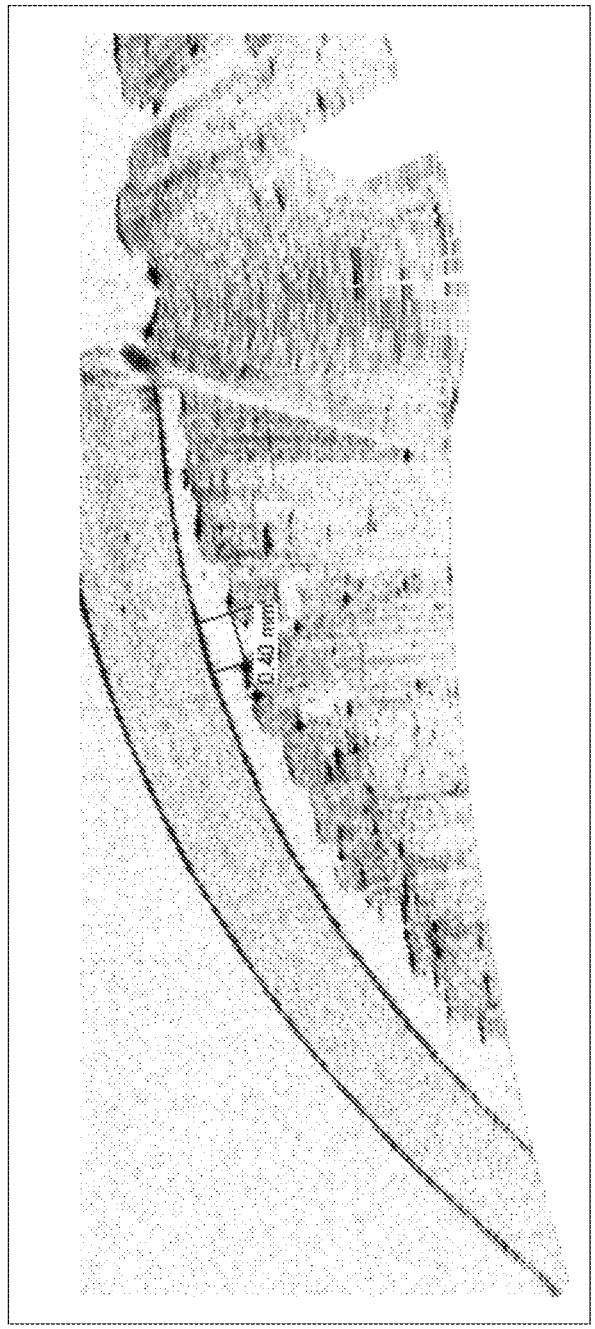
FIG. 28.—Ultrasound image illustrating a cell example in parallels B and I with vertical measurement in model C-100 of 18 mm in its longest size.

The plurality of poles, nodes and angles facilitate suturing; and has the advantage of decreasing time in the operating room. In contrast, the implants commercially available have settled specific tunnels for suturing in clamping, and they are complicated and limited. In the case of the present invention, it represents an inventive novelty, the arrangement of multicells with poles and nodes is distinguished by its great versatility that efficiently solves this procedure. A clear example is the 18 mm diameter implant of the C-100 model that has 20 cells in its largest size (E and F) of 3.20 mm by 1.50 mm (FIG. 21, FIG. 22); 20 cells (D and G) of 2.70 mm by 1.40 mm (FIG. 23, FIG. 24); 20 cells (C and H) of 1.75 mm by 1.00 mm (FIG. 25 FIG. 26); 20 cells (B and I) of 0.65 mm by 0.40 mm (FIGS. 27 and 28).

The poles and nodes described are identifiable in each cell, which as described is nominated according to its Cartesian location (with the corresponding parallel letter and the number of the meridian) in such a way that each pole receives the determinant "p" and each node, the determinant "n". The number of each pole is defined according to its clockwise position, number 1 being the upper (12 on the clock hands); the nodes are identified according to the same procedure (FIG. 4).

The suturing described above is applicable in cases of evisceration, i.e. casting of the eyeball with scleral shell preservation escleralthe Nucleo-reticular Multi-cell Dual-system Eye Implant allows an excellent suturing clamping to the sclera and can be attached thereto or even encompass such suturing to the available extraocular muscles, whereby there is an increase in clamping and mobility with greater use of scleral tissue (FIG. 20, Ref. 1).

Vascularizable

The design of the structures in the MMM and FRC systems has the function of increasing the volume of blood flow or vascular integration as it is an open duct implant.

The outer structure of the MMM system makes vascularization immediately flood (FIG. 10) permeating the FRC system, whose micro-reticular multilevels (FIG. 7, Ref. 1) and filaments (FIGS. 12 and 7, Ref. 2) in intra-level spaces generate the ideal conditions for immediate and frank blood irrigation during surgery, and with short-term effects regarding the generation of fibrovascular tissue, which is favored with the support that the Reticular Fibrovascular Core System provides.

Figure 10:
FIG. 10.—Illustrates a photograph of fibro vascularized spherical structure in a patient.

One of the main contributions that represent novelty and inventive to the Nucleo-reticular Multi-cell Dual-system Eye Implant consists of immediate vascular flooding, provable in the first seconds of its placement in surgical time by the oculoplastic surgeon (FIG. 10). In addition, the previous process in porous implants, the vascularization is not immediate, controllable or verifiable in surgical time, without certainty of the success of vascularization and integration.

The C-100 model is cited in a 18 mm diameter with a design of 100 oval multicells, (FIG. 18) which presents in its largest size, 20 cells (E and F) of 3.20 mm by 1.50 mm (FIG. 21, FIG. 22); 20 cells (D and G) of 2.70 mm by 1.40 mm (FIG. 23, FIG. 24); 20 cells (C and H) of 1.75 mm by 1.00 mm (FIG. 25 FIG. 26); 20 cells (B and I) of 0.65 mm by 0.40 mm (FIGS. 27 and 28), which together allow the vasculating function. Said initial model of 18 millimetres (mm) in diameter has a volume of 3.05 milliliters (ml). The density of polylactic acid (PLA) is 1.25 grams/cubic centimeter (gr/cm$^3$), if it were a solid sphere, it would weigh 3.81 gr. However, thanks to the design of the Multi-cell and Nucleo-reticular systems and polylactic acid (PLA) material, a weight of only 1.48 gr is reached, and the percentage obtained for the volume to be vascularized is 61.22%. This reached volume allows the growth of the tissues therein, which favors and accelerates its fibrovascular integration and minimizes the risks of extrusion and rejection in the short and medium term. The design of the Nucleo-reticular Multi-cell Dual-system Eye Implant promotes and accelerates fibrovascular increase during the healing process, which increases biological integration, reduces the risk of infection and achieves a better mechanical integration with neighboring tissues. This new generation of structural implants manage to integrate the tissue that grows within the Core of the sphere, so blood cells and medicines can circulate by having internal fibrovascular growth.

With the measurements of the structure of the model C100 implant, manufactured with polylactic acid (PLA), which has a density of 1.25 gr/cm$^3$, the best results of measurement-to-weight ratio are achieved, the same as referred to in the table in FIG. 29 and provable by the following equation:

Volume of the Celled Sphere $d=m/v$ $m=1.48\ g \rightarrow$ celled sphere mass $d=1.25\ g/cm^3$ $v=m/d=1.48\ g/1.25\ g/cm^3 - 1,184\ cm^3$ (cell volume·Total sphere)

Solid Volume=3.0536 cm$^3$

Material volume PLA=1.184 cm$^3$

Free Volume=3.0536→100%

Volume to be filled=1.8696 cm$^3$

PLA $x$=1.8696 cm$^3$(100%)/3.0536 cm$^3$ material(solid sphere)=61.22%

Biocompatible Material

The Nucleo-reticular Multi-cell Dual-system Eye Implant of calculated axial length filed for patent, can be manufactured with multiple materials, synthetic or natural, inert, provided that they are biocompatible and harmless. The structural capacity of the exhibited design presented has conditions to be manufactured with materials of natural or synthetic origin, in a molded, pressed, emptied, by stereolithography or any other that are experimentally designed and integrated.

In the different models, polylactic acid (PLA) has been used as it is a material that does not present rejection by the body, with ideal density, weight and accessibility, being highly biocompatible. The material used in all models of the multi-cell structural implants is a "polymer made up of lactic acid molecules, with properties similar to those of polyethylene terephthalate (PET). It has been previously used (since the 1960 s) in a variety of medical and surgical applications such as suturing material (reabsorbable thread), orthopedic materials (such as screws and plates) and implants. The polylactic acid has become an essential material in medical industry, where it has been used for years. As polylactic acid is a biodegradable and bioabsorbable polymer (i.e., it can be assimilated by our biological system), PLA is an ideal candidate for bone or tissue implants (orthopedic surgery, ophthalmology, orthodontics, controlled launch of cancer drugs), and for suturing (eye surgery, chest and abdomen surgery)."[5].

Motor Skills

The Muscular Motor Multi-cell system (MMM) takes advantage of the arrangement of agonist and antagonistic muscles and/or scleral tissue, which determine natural movement; in connection with enucleative and evisceral injuries (FIGS. 19 and 20) where the eyeball is damaged, and the muscular striatum still gradually retains its functionality. With this invention having a multi-cell spherical structure, it is possible to increase the mobility threshold with variable suturing.

Figure 19:
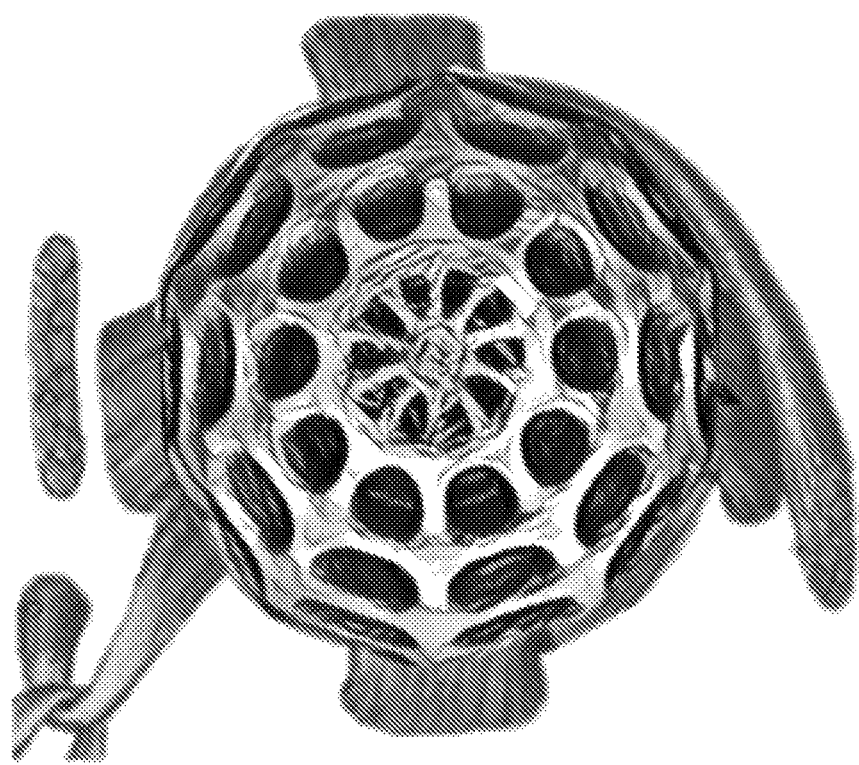
FIG. 19.—Illustrates the Nucleo-reticular Multi-cell Dual-system Eye Implant in case of frontal enucleation with muscle evidence suture.

The implant of the present invention, in its model type C-100, contains a structure of 100 oval multicells, of which 80 (FIG. 5, Ref. 1) (from B to I) are useful specifically for comforming to any suturing method, with 150 clamping poles (FIG. 5, Ref. 2) and 70 nodes (FIG. 5, Ref. 3) with multiple angles and distances, (FIGS. 5 and 11) that manage to reposition available extraocular muscles (FIG. 19).

Figure 1:
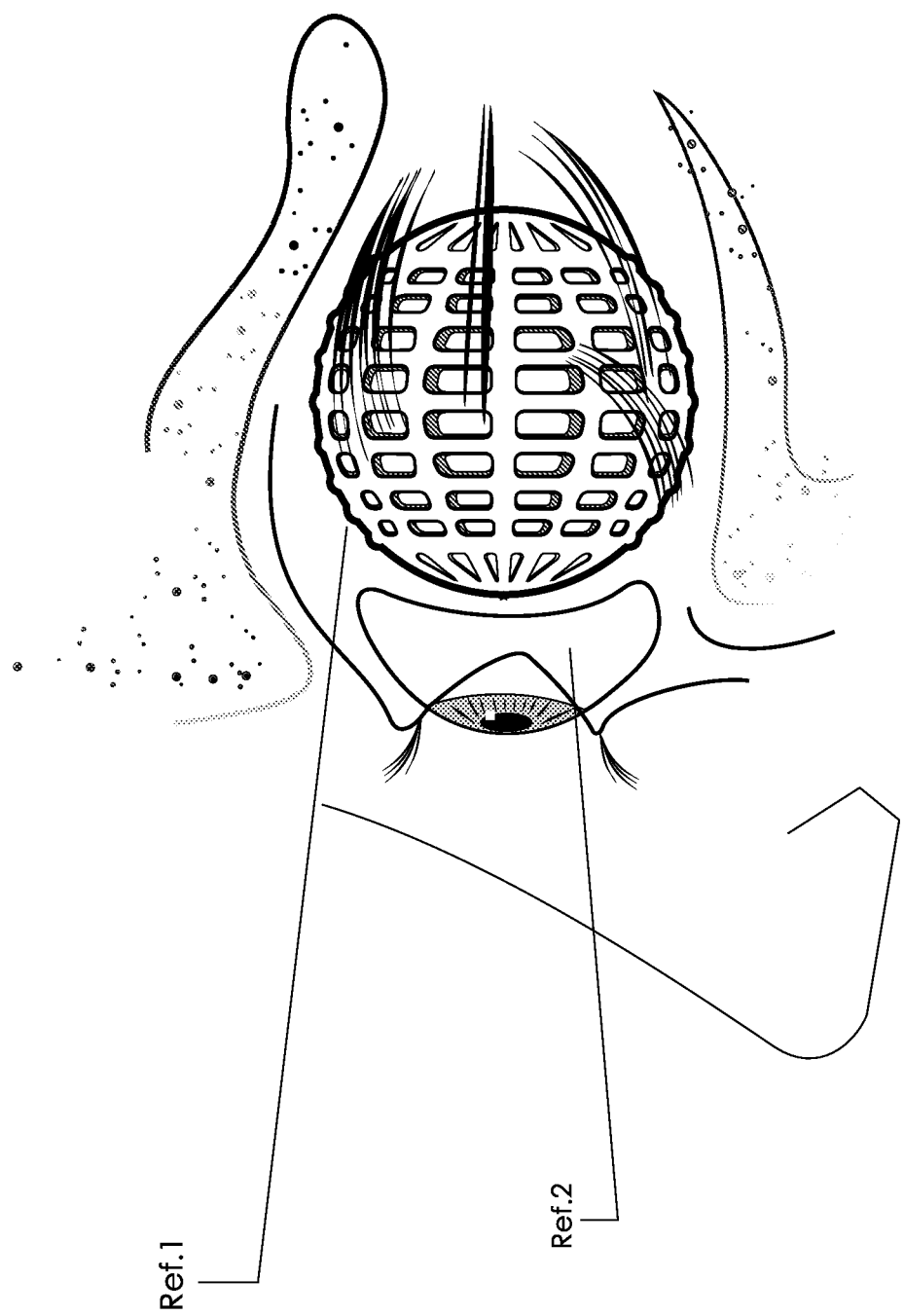
FIG. 1.—Illustrates the implant scheme (Ref. 1) with prosthesis (Ref. 2) in eye socket, side image.
Figure 2:
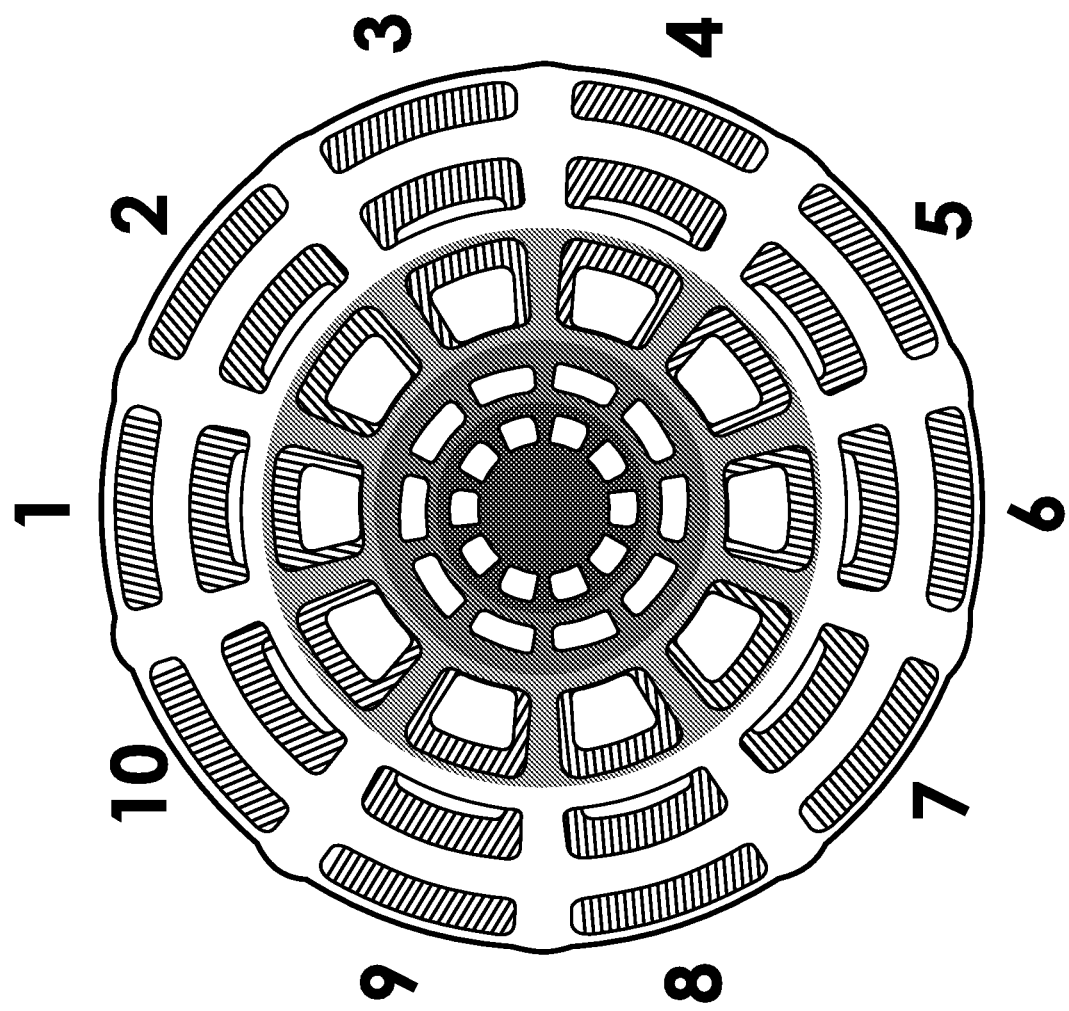
FIG. 2.—Illustrates the front view of the multi-cell spherical structure. A structure with cells formed in order of tens can be seen.

Using the poles and nodes that define the multicells to hold the muscles with the sutures with increased efficiency and higher expectations of mobility, a better integration is allowed to help in the voluntary mobility of basal structures that integrate with the implant, which generates a greater range of mobility to implants (FIG. 1, Ref. 1) that support the aesthetic ocular prostheses (FIG. 1, Ref. 2) aesthetic prosthesis, the same that transcends movement.

Due to the availability created by the multicells of the MMM system, the implant clamping process has conditions that favor the suturing with wide margin of technical and operational resources, the surgeon being able to identify the most suitable poles and/or nodes of the multicells, achieving the precision in the identification of the suture points, obtaining greater performance by having the availability for direct fixation to the extraocular muscles.

The implant filed for patent has a multi-cell scheme with Cartesian location (FIG. 14), with poles and nodes identifiable by an ordinal number, which gives the surgeon the option of having detailed protocols of each surgery, which, if applicable, allows to accumulate the experiences acquired from each process, or in specific cases, to schedule maintenance or corrective surgeries with a high margin of precision, which represents a novelty based on an inventive process that meets the greatest requirements.

In the C-100 model based on the 100 oval multi-cell scheme there are 80 useful cells with poles and nodes identifiable for suturing, being the suggested implant a device that increases the possibilities of muscle clamping, providing suturing variability. Models of different design and number of cells can be selected according to the specific conditions of the receiving patient.

The invention claimed is:

1. A Nucleo-reticular Multi-cell Dual-system Eye Implant, comprising a Muscular Motor Multi-cell System (MMM) eye implant as an outer structure, the MMM comprising a substantially spherical structure of cells having an axial length, an inner space, and lineal structures of transverse and vertical poles, said lineal structures being interconnected with each other at the cross-section of two or more poles to form a node and defining a plurality of cells distributed throughout, each cell provides an opening to the inner space of the structure of cells, wherein the Nucleo-reticular Multi-cell Dual-system Eye implant also comprises an inner Reticular Fibrovascular Nucleus system (NRF) structure, the NRF structure comprising micro-reticular mesh platforms separated by fibrous structures.

2. The implant of claim 1, wherein the structure of cells is spherical.

3. The implant of claim 2, wherein each cell on the structure of cells is identifiable by cartesian coordinates consisting of a parallel coordinate defined with a letter and a meridian coordinate defined with a number; the meridian being parallel to the axial length and the parallel being perpendicular to the axial length.

4. The implant of claim 1, wherein the poles are configured to support vertical and horizontal sutures between said dual-system eye implant and antagonist/agonist muscles or/and scleral tissue.

5. The implant of claim 1, wherein the nodes are configured to support diagonal sutures between said MMM and antagonist/agonist muscles or/and scleral tissue.

6. The implant of claim 1, wherein the micro-reticular platforms are organized in multilevels parallel to each other and perpendicular to the axial length of the substantially spherical structure of cells.

7. The implant of claim 1, wherein the fibrous structures fill the inner space between said micro-reticular platforms.

8. The implant of claim 1, comprising a natural or synthetic biocompatible material selected from the group consisting of metal, polymer, organic, plant and cellular material.

9. The implant of claim 8, wherein the biocompatible material is polylactic acid.

10. The implant of claim 9, wherein the polylactic acid has a density of 1.25 g/cm$^3$.

11. The implant of claim 1, wherein the NRF comprises a natural or synthetic biocompatible material selected from the group consisting of ceramic, metal, polymer, organic, plant and cellular material.

12. The implant of claim 11, wherein the biocompatible material is polylactic acid.

13. The implant of claim 12, wherein the polylactic acid has a density of 1.25 g/cm$^3$.

14. The implant of claim 1, manufactured by a process selected from the group consisting of molding, casting, die-cutting, injecting, cast pressing, weaving, sublimation, cell induction and stereolithography.

15. A method of filling an orbital space or eye socket after evisceration or enucleation of the eyeball comprising implanting the implant of claim 1 into the orbital space or eye socket.

* * * * *